(12) United States Patent
Nishimura et al.

(10) Patent No.: US 8,455,444 B2
(45) Date of Patent: Jun. 4, 2013

(54) CDH3 PEPTIDE AND MEDICINAL AGENT COMPRISING THE SAME

(75) Inventors: Yasuharu Nishimura, Kumamoto (JP); Katsunori Imai, Kumamoto (JP); Takuya Tsunoda, Kanagawa (JP); Yusuke Nakamura, Tokyo (JP)

(73) Assignee: Oncotherapy Science, Inc., Kanagawa (JP)

( * ) Notice: Subject to any disclaimer, the term of this patent is extended or adjusted under 35 U.S.C. 154(b) by 150 days.

(21) Appl. No.: 12/673,451

(22) PCT Filed: Jun. 5, 2008

(86) PCT No.: PCT/JP2008/060381
§ 371 (c)(1),
(2), (4) Date: Oct. 22, 2010

(87) PCT Pub. No.: WO2009/025116
PCT Pub. Date: Feb. 26, 2009

(65) Prior Publication Data
US 2011/0165184 A1    Jul. 7, 2011

(30) Foreign Application Priority Data
Aug. 20, 2007   (JP) .................................. 2007-213999

(51) Int. Cl.
*A61K 38/00* (2006.01)
*C07K 7/00* (2006.01)

(52) U.S. Cl.
USPC .......................... 514/19.2; 514/19.3; 530/325

(58) Field of Classification Search
None
See application file for complete search history.

(56) References Cited

U.S. PATENT DOCUMENTS

| | | | |
|---|---|---|---|
| 5,891,432 A * | 4/1999 | Hoo | 424/93.21 |
| 6,169,071 B1 | 1/2001 | Blaschuk et al. | |
| 6,551,795 B1 * | 4/2003 | Rubenfield et al. | 435/69.1 |
| 6,699,703 B1 * | 3/2004 | Doucette-Stamm et al. | 435/252.3 |
| 6,747,137 B1 * | 6/2004 | Weinstock et al. | 536/23.1 |
| 7,033,832 B2 * | 4/2006 | Nackman et al. | 435/395 |
| 7,122,331 B1 * | 10/2006 | Eisenreich et al. | 435/7.4 |
| 7,214,786 B2 * | 5/2007 | Kovalic et al. | 536/23.6 |
| 7,314,974 B2 * | 1/2008 | Cao et al. | 800/289 |
| 7,745,391 B2 * | 6/2010 | Mintz et al. | 514/19.3 |
| 7,960,608 B2 * | 6/2011 | Mouradov et al. | 800/278 |
| 8,088,976 B2 * | 1/2012 | Boukharov et al. | 800/285 |
| 2003/0086934 A1 | 5/2003 | Botstein et al. | |
| 2003/0148314 A1 | 8/2003 | Berger et al. | |
| 2005/0214836 A1 | 9/2005 | Nakamura et al. | |
| 2005/0259483 A1 | 11/2005 | Nakamura et al. | |
| 2005/0260639 A1 | 11/2005 | Nakamura et al. | |
| 2006/0024692 A1 | 2/2006 | Nakamura et al. | |
| 2006/0105333 A1 | 5/2006 | Nakamura et al. | |
| 2006/0194199 A1 | 8/2006 | Nakamura et al. | |
| 2006/0199179 A1 | 9/2006 | Nakamura et al. | |
| 2006/0240001 A1 | 10/2006 | Bauer et al. | |
| 2006/0270619 A1 | 11/2006 | Nakamura et al. | |
| 2007/0037204 A1 | 2/2007 | Aburatani et al. | |
| 2009/0162361 A1 | 6/2009 | Nakamura et al. | |
| 2009/0169572 A1 | 7/2009 | Nakatsuru et al. | |
| 2009/0175844 A1 | 7/2009 | Nakamura et al. | |
| 2010/0040641 A1 * | 2/2010 | Tsunoda et al. | 424/185.1 |
| 2012/0014996 A1 | 1/2012 | Nakamura et al. | |

FOREIGN PATENT DOCUMENTS

| | | |
|---|---|---|
| EP | 1806359 A1 | 7/2007 |
| JP | 2006-500947 A | 1/2006 |
| JP | 2007-224009 A | 9/2007 |
| RU | 2009/135020 A | 3/2011 |
| WO | WO 02/08765 A2 | 1/2002 |
| WO | WO 02/086443 A2 | 10/2002 |
| WO | WO 02/097395 A2 | 12/2002 |
| WO | WO 04/001072 A2 | 12/2003 |
| WO | WO 2004/007770 A2 | 1/2004 |
| WO | WO 2004/031410 A2 | 4/2004 |
| WO | WO 2004/031411 A2 | 4/2004 |
| WO | WO 2004/031412 A2 | 4/2004 |
| WO | WO 2004/031413 A2 | 4/2004 |
| WO | WO 2004/031414 A2 | 4/2004 |
| WO | WO 2004/035732 A2 | 4/2004 |
| WO | WO 2004/110345 A2 | 12/2004 |
| WO | 2005/090572 A2 | 9/2005 |
| WO | 2006/090810 A2 | 8/2006 |
| WO | WO 2006/085684 A2 | 8/2006 |
| WO | WO 2006/114704 A2 | 11/2006 |
| WO | 2007/009181 * | 1/2007 |
| WO | WO 2007/013575 A2 | 2/2007 |
| WO | WO 2007/102525 A1 | 9/2007 |
| WO | 2008/047473 * | 4/2008 |
| WO | WO 2008/102557 A1 | 8/2008 |

OTHER PUBLICATIONS

Johnson et al, Cancer Treatment Reviews vol. 2 p. 1 (1975).*
Essell (J. NIH Res. 1995 7:46).*
Boon (Adv. Can. Res. 1992 58:177-210).*
Burgess et al, Journal of Cell Biology vol. 111 Nov. 1990 2129-2138.*
Lazar et al Molecular and Cellular Biology Mar. 1988 vol. 8 No. 3 1247-1252.*
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

(Continued)

*Primary Examiner* — Sheela J Huff
(74) *Attorney, Agent, or Firm* — Kilpatrick Townsend & Stockton LLP

(57) ABSTRACT

The present invention provides a peptide of the following (A) or (B):
(A) a peptide including an amino acid sequence of SEQ ID NO: 1 or 2;
(B) a peptide including an amino acid sequence of SEQ ID NO 1 or 2, wherein one, two, or several amino acid(s) are substituted, deleted, inserted, and/or added, and wherein the peptide has an activity to induce killer T cells.

11 Claims, 5 Drawing Sheets

OTHER PUBLICATIONS

Falk, et al., "Allele-specific motifs revealed by sequencing of self-peptides eluted from MHC molecules," *Nature*, vol. 351(6324), pp. 290-296 (May 23, 1991).

Hoffman, et al., "The Ability of Variant Peptides to Reverse the Nonresponsiveness of T Lymphocytes to the Wild-Type Sequence p53$_{264-272}$ Epitope," *J Immunol.*, vol. 168(3), pp. 1338-1347 (Feb. 1, 2002).

Rammensee, et al., "MHC ligands and peptide motifs: first listing," *Immunogenetics*, vol. 41(4), pp. 178-228 (1995).

Stevanovic, "Identification of Tumour-Associated T-Cell Epitopes For Vaccine Development," *Nat Rev Cancer*, vol. 2(7), pp. 514-520 (Jul. 2002).

U.S. Appl. No. 13/001,869, which is a U.S. National Phase (371) of PCT/JP2009/003009, 62 pgs.

U.S. Appl. No. 13/464,831, filed May 4, 2012, 163 pages.

Adams, et al., "Prediction of binding to MHC class I molecules," *J Immunol Methods*, vol. 185(2), pp. 181-190 (Sep. 25, 1995).

Ashida, et al., "Molecular Features of the Transition from Prostatic Intraepithelial Neoplasia (PIN) to Prostate Cancer: Genome-wide Gene-expression Profiles of Prostate Cancers and PINs," *Cancer Res.*, vol. 64(17), pp. 5963-5972 (Sep. 1, 2004).

Behrens, "Cadherins and catenins: Role in signal transduction and tumor progression," *Cancer Metastasis Rev.*, vol. 18(1), pp. 15-30 (1999).

Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).

Belokoneva, "Immunity Retro Style," *Science and Life 1*, pp. 45-48 (2004).

Bienz, et al., "Linking Colorectal Cancer to Wnt Signaling Review," *Cell*, vol. 103(2), pp. 311-320 (Oct. 13, 2000).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Conacci-Sorrell, et al., "The cadherin-catenin adhesion system in signaling and cancer," *J Clin Invest.*, vol. 109(8), pp. 987-991 (Apr. 2002).

Coulie, et al., "Cytolytic T-cell responses of cancer patients vaccinated with a MAGE antigen," *Immunol Rev.*, vol. 188, pp. 33-42 (Oct. 2002).

Fujie, et al., "A Mage-1-Encoded HLA-A-A24-Binding Synthetic Peptide Induces Specific Anti-Tumor Cytotoxic T Lymphocytes," *Int J Cancer*, vol. 80(2), pp. 169-172 (Jan. 18, 1999).

Gross, et al., "High vaccination efficiency of low-affinity epitopes in antitumor immunotherapy," *J Clin Invest.*, vol. 113(3), pp. 425-433 (Feb. 2004).

Harris, Structure and Function of the p53 Tumor Suppressor Gene: Clues for Rational Cancer Therapeutic Strategies, *J Natl Cancer Inst.*, vol. 88(20), pp. 1442-1455 (Oct. 16, 1996).

Imai, et al., Identification of a Novel Tumor-Associated Antigen, Cadherin 3/P-Cadherin, as a Possible Target for Immunotherapy of Pancreatic, Gastric, and Colorectal Cancers, *Clin Cancer Res.*, vol. 14(20), pp. 6487-6495 (Oct. 15, 2008).

Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Lin, et al., "Molecular diagnosis of colorectal tumors by expression profiles of 50 genes expressed differentially in adenomas and carcinomas," *Oncogene*, vol. 21(26), pp. 4120-4128 (Jun. 13, 2002).

Nose, et al., "A Novel Cadherin Cell Adhesion Molecule: Its Expression Patterns Associated with Implantation and Organogenesis of Mouse Embryos," *J Cell Biol.*, vol. 103(6 Pt 2), pp. 2649-2658 (Dec. 1986).

Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).

Okabe, et al., "Genome-wide Analysis of Gene Expression in Human Hepatocellular Carcinomas Using cDNA Microarray: Identification of Genes Involved in Viral Carcinogenesis and Tumor Progression," *Cancer Res.*, vol. 61(5), pp. 2129-2137 (Mar. 1, 2001).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Rosenberg, et al., "Cancer Immunotherapy: moving beyond current vaccines," *Nat Med.*, vol. 10(9), pp. 909-915 (Sep. 2004).

Schueler-Furman, et al., "Structure-based prediction of binding peptides to MHC class I molecules: Application to a broad range of MHC alleles," *Protein Sci.*, vol. 9(9), pp. 1838-1846 (Sep. 2000).

Takeichi, "The cadherins: cell-cell adhesion molecules controlling animal morphogenesis," *Development*, vol. 102(4), pp. 639-655 (Apr. 1988).

Takeichi, "Cadherin Cell Adhesion Receptors as a Morphogenetic Regulator," *Science*, vol. 251(5000), pp. 1451-1455 (Mar. 22, 1991).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Yasui, et al., "Expression of P-Cadherin in Gastric Carcinomas and its Reduction in Tumor Progression," *Int J Cancer*, vol. 54(1), pp. 49-52 (Apr. 22, 1993).

GenBank: Accession No. EAW83239.1, G1: 119603645, 2 pages (Dec. 18, 2006).

Protein sequence analysis, http://vitalonic.narod.ru/biochem/index. html, 2 pages (last modified Jan. 14, 2006).

U.S. Appl. No. 60/902,949, 93 pages, filed Feb. 21, 2007.

U.S. Appl. No. 13/519,127, which is a U.S. National Stage of PCT/JP2009/007333, 59 pages, filed Dec. 28, 2009.

U.S. Appl. No. 13/536,327, 204 pages, filed Jun. 28, 2012.

Roitt, et al., Immunology, M: Mir, pp. 159, 160-162 (2000).

Wadler, S., "Molecular Targeting in Pancreatic Cancer," *Reviews on Recent Clinical Trials*, vol. 2(1), pp. 69-75 (Jan. 2007).

Bauer, R., et al., "Functional implication of truncated P-cadherin expression in malignant melanoma," *Exp. Mol. Pathol.*, vol. 81(3), pp. 224-230 (Dec. 2006).

Chen, G., et al., "Identification of the Cadherin Subtypes Present in the Human Peritoneum and Endometriotic Lesions: Potential Role for P-Cadherin in the Development of Endometriosis," *Mol. Reprod. Dev.*, vol. 62(3), pp. 289-294 (Jul. 2002).

Christofori, G., et al., "Changing neighbours, changing behaviour: cell adhesion molecule-mediated signaling during tumour progression," *EMBO*, vol. 22(10), pp. 2318-2323 (May 15, 2003).

Gamallo, C., et al., "The Prognostic Significance of P-Cadherin in Infiltrating Ductal Breast Carcinoma," *Mod. Pathol.*, vol. 14(7), pp. 650-654 (Jul. 2001).

Harada, M., et al., "Kinesin superfamily protein-derived peptides with the ability to induce giloma-reactive cytotoxic T lymphocytes in human leukocyte antigen-A24[+] giloma patients," *Oncol. Rep.*, vol. 17(3), pp. 629-636 (Mar. 2007).

Imai, K., et al., "CDH3, a novel cancer-associated antigen useful for immunotherapy of pancreatic cancer," *The 66th Annual Meeting of the Japanese Cancer Association*, p. 164, Abstract: #P-296 (Aug. 25, 2007).

Imai, et al., "Identification of new useful oncoantigen CDH3 for immunotherapy in pancreatic cancer," *Journal of Japan Surgical Society*, vol. 109(special extra issue 2), p. 529, Abstract: #DP-093-1 (Apr. 25, 2008).

Ishikawa, N., et al., "Cancer-Testis Antigen Lymphocyte Antigen 6 Complex Locus K Is a Serologic Biomarker and a Therapeutic Target for Lung and Esophageal Carcinomas," *Cancer Res.*, vol. 67(24), pp. 11601-11611 (Dec. 15, 2007).

Jankowski, J., et al., "Alterations in Classical Cadherins Associated with Progression in Ulcerative and Crohn's Colitis," *Lab. Invest.*, vol. 78(9), pp. 1155-1167 (Sep. 1998).

Komori, H., et al., "Identification of HLA-A2- or HLA-A24-Restricted CTL Epitopes Possibly Useful for Glypican-3-Specific Immunotherapy of Hepatocellular Carcinoma," *Clin. Cancer Res.*, vol. 12(9), p. 2689-2697 (May 1, 2006).

Kondo, A., et al., "Prominent Roles of Secondary Anchor Residues in Peptide Binding to HLA-A24 Human Class I Molecules," *J. Immunol.*, vol. 155(9), pp. 4307-4312 (Nov. 1, 1995).

Kovacs, A., et al., "P-cadherin as a marker in the differential diagnosis of breast lesions," *J. Clin. Pathol.*, vol. 56(2), pp. 139-141 (Feb. 2003).

Kubo, R., et al., "Definition of Specific Peptide Motifs for Four Major HLA-A Alleles," *J. Immunol.*, vol. 152(8), pp. 3913-3924 (Apr. 15, 1994).

Munoz-Guerra, M., et al., "P-Cadherin Expression Reduced in Squamous Cell Carcinoma of the Oral Cavity," *Cancer*, vol. 103(5), pp. 960-969 (Mar. 1, 2005).

Nakagawa, H., et al., "Over-expressed P-cadherin/CDH3 promotes motility of pancreatic cancer cells by interacting with p120ctn and activating Rho-family GTPases," AACR Meeting Abstracts, 546 (Apr. 2005).

Nakamura, T., et al., "Genome-wide cDNA microarray analysis of gene expression profiles in pancreatic cancers using populations of tumor cells and normal ductal epithelial cells selected for purity by laser microdissection," *Oncogene*, vol. 23(13), pp. 2385-2400 (Mar. 25, 2004).

Nose, A., et al., Isolation of placental cadherin cDNA: identification of a novel gene family of cell-cell adhesion molecules, *EMBO*, vol. 6(12), pp. 3655-3661 (Dec. 1, 1987).

Obama, K., et al., "Genome-Wide Analysis of Gene Expression in Human Intrahepatic Cholangiocarcinoma," *Hepatology*, vol. 41(6), pp. 1339-1348 (Jun. 2005).

Paredes, J., et al., "P-Cadherin Overexpression Is an Indicator of Clinical Outcome in Invasive Breast Carcinomas and Is Associated with *CDH3* Promoter Hypomethylation," *Clin. Cancer Res.*, vol. 11(16), pp. 5869-5877 (Aug. 15, 2005).

Radice, G., et al., "Precocious Mammary Gland Development in P-Cadherin-deficient Mice," *J. Cell Biol.*, vol. 139(4), pp. 1025-1032 (Nov. 17, 1997).

Shimoyama, Y., et al., "Cadherin Cell-Adhesion Molecules in Human Epithelial Tissues and Carcinomas," *Cancer Res.*, vol. 49(8), pp. 2128-2133 (Apr. 15, 1989).

Shimoyama, Y., et al., "Expression of E- and P-Cadherin in Gastric Carcinomas," *Cancer Res.*, vol. 51(8), pp. 2185-2192 (Apr. 15, 1991).

Shimoyama, Y., et al., "Molecular Cloning of a Human $Ca^{2+}$-dependent Cell-Cell Adhesion Molecule Homologous to Mouse Placental Cadherin: Its Low Expression in Human Placental Tissues," *J. Cell Biol.*, vol. 109(4 Pt 1), pp. 1787-1794 (Oct. 1989).

Soler, A., et al., "P-Cadherin Expression in Breast Carcinomas Indicates Poor Survival," *Cancer*, vol. 86(7), pp. 1263-1272 (Oct. 1, 1999).

Stefansson, I., et al., "Prognostic Impact of Alterations in P-Cadherin Expression and Related Cell Adhesion Markers in Endometrial Cancer," *J. Clin. Oncol.*, vol. 22(7), pp. 1242-1252 (Apr. 1, 2004).

Suda, T., et al., "Identification of human leukocyte antigen-A-restricted epitope peptides derived from gene products upregulated in lung and esophageal cancers as novel targets for immunotheraphy," *Cancer Sci.*, vol. 98, pp. 1803-1808 (Sep. 2, 2007).

Suda, T., et al., "Identification of *secernin 1* as a novel immunotherapy target for gastric cancer using the expression profiles of cDNA microarray," *Cancer Sci.*, vol. 97(5), pp. 411-419 (May 2006).

Taniuchi, K., et al., "Overexpressed P-Cadherin/CDH3 Promotes Motility of Pancreatic Cancer Cells by Interacting with p120ctn and Activating Rho-Family GTPases," *Cancer Res.*, vol. 65(8), pp. 3092-3099 (Apr. 15, 2005).

Van Marck, V., et al., "P-Cadherin Promotes Cell-Cell Adhesion and Counteracts Invasion in Human Melanoma," *Cancer Res.*, vol. 65(19), pp. 8774-8783 (Oct. 1, 2005).

Zaremba, S., et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).

U.S. Appl. No. 13/744,354, filed Jan. 17, 2013, 124 pages.

Denzer, et al., "Exosome: from internal vesicle of the multivesicular body to intercellular signaling device," *J Cell Sci.*, vol. 113, Pt 19, pp. 3365-3374 (Oct. 2000).

Roitt, et al., Immunology, translation from English, M: Mir; pp. 194-199 (2000).

* cited by examiner

US 8,455,444 B2

CDH3 PEPTIDE AND MEDICINAL AGENT COMPRISING THE SAME

CROSS-REFERENCES TO RELATED APPLICATIONS

The present application is a U.S. National Phase of PCT/JP2008/060381, filed Jun. 5, 2008, which claims the benefit of Japanese Application No. 2007-213999, filed on Aug. 20, 2007, the disclosures of which are hereby incorporated herein by reference in their entirety.

TECHNICAL FIELD

The present invention relates to novel peptides useful as vaccines against cancers highly expressing P-cadherin (CDH3) such as pancreatic cancer, cholangiocellular carcinoma, gastric cancer, colon cancer, and lung cancer, and to pharmaceutical agents including the peptide for treating and preventing cancer.

BACKGROUND ART

Pancreatic cancer accounts for approximately 2 to 3% of all malignant tumors. Every year, about 200,000 people around the world die from pancreatic cancer, and its death toll is the 5th largest in malignant tumors. In Japan, about 20,000 people die annually. Risk factors for pancreatic cancer development include diabetes, chronic pancreatitis, smoking, and the like, and family history has also been reported to be one of the risk factors. Various attempts of early diagnosis have been made, including improvement of diagnostic imaging; however, most of the patients are diagnosed at advanced stages when they show resistance to chemotherapy. Thus, their five-year survival rate is about 9.7%, and only about 13% even in surgically-removed cases. Pancreatic cancer results in the most unfavorable prognosis among digestive system cancers. Due to this difficulty in diagnosis, there is a gradual increase in the incidence of pancreatic cancer as a cause of cancer death, especially in developed countries. Although multidisciplinary treatments, primarily surgical resection, and other treatments such as radiotherapy and chemotherapy are being carried out, they have not dramatically improved therapeutic effects, and novel therapeutic strategies are urgently needed.

Cholangiocellular carcinoma accounts for about 10% of primary liver cancer, and is the second most common cancer, following hepatocellular carcinoma. It shows poor clinical characteristics, and in many cases, the cancer is detected at advanced stages accompanying lymph node metastasis, intrahepatic metastasis, and the like. The five-year survival rate is about 20%, and is 35% in surgically-removed cases, but is very poor, only 7.4%, in surgically unremoved cases. Although surgical resection is the only therapy that can be expected to lead to long-term survival, many patients are already inoperable at the time of detection (rate of surgery: 66%, noncurative resection rate: 20%). Both anticancer drug sensitivity and radiosensitivity of patients are low, and the establishment of a therapy for inoperable cases, including noncurative resection cases, has been desired.

Compared to Western countries, morbidity rate of gastric cancer is high in Asian nations, such as Japan and China. Early detection of gastric cancer has become possible by the spread of medical tests, and progress of digestive endoscopic instruments and inspection techniques, hence decreasing the number of patients. However, gastric cancer is still the second leading cause of death in malignant neoplasms among Japanese, and its rate in cause of death is still high. Colon cancer is the second most common cancer in Western countries, and is the third most common cause of death in malignant neoplasms in Japan. Gastric cancer and colon cancer are treated mainly by surgical resection, and also by chemotherapy, radiotherapy, and the like. Immunotherapy that suppresses cancer growth by improving the immunity of the cancer patient against the cancer is attracting attention as a novel therapy for metastatic cancer and intractable cancer, against which, application of the previously mentioned therapies is impossible.

Lung cancer is continuously increasing in recent years around the world, and currently, about one million people die of lung cancer in a year. Lung cancer death is continuously increasing also in Japan and is thought to reach 123,000 in 2015. It is the leading cause of death in malignant neoplasms in Japan. The number of patients is thought to increase as the aging of the population progresses. Early detection and early treatment are important in lung cancer treatment. However, it has recently been pointed out that simple chest x-rays and sputum tests conducted in health checks have poor effects on the early detection of lung cancer, and do not lead to reduction of cancer deaths. Since the number of deaths from lung cancer is considered to continuously increase, development of a novel therapeutic strategy is an urgent challenge.

On the other hand, recent developments in molecular biology and tumor immunology have elucidated that cytotoxic (killer) T cells and helper T cells recognize peptides generated by degradation of proteins that are specifically and highly expressed in cancer cells and which are presented on the surface of cancer cells or antigen presenting cells via HLA molecules, and cause an immunoreaction that destroys cancer cells. Further, many tumor antigen proteins and peptides derived therefrom, which stimulate such immunoreactions that attack these cancers, have been identified, and clinical application of antigen-specific tumor immunotherapies are now in progress.

HLA class I molecule is expressed on the surface of all nucleated cells of the body. It is expressed on the cell surface by binding to peptides generated by intracellular degradation of proteins produced in the cytoplasm or in the nucleus. On the surface of a normal cell, peptides derived from its normal proteins are bound to HLA class I molecules, and the T cells of the immune system will not identify them to destroy the cell. On the other hand, in the process of canceration, cancer cells sometimes express a large amount of proteins which are hardly or very slightly expressed in normal cells. When the HLA class I molecules bind to peptides generated by intracellular degradation of proteins specifically and highly expressed in cancer cells and then expressed on the surface of cancer cells, killer T cells will recognize them and destroy only the cancer cells. Moreover, by administering such cancer-specific antigens or peptides to an individual, an immune response that destroys cancer cells and suppresses cancer growth can be induced without harming normal cells. This is called cancer immunotherapy using cancer-specific antigens. HLA class II molecules are mainly expressed on the surface of antigen presenting cells. HLA class II molecules bind to peptides derived from cancer-specific antigens, which are generated by intracellular degradation of cancer-specific antigens incorporated into antigen presenting cells from outside of the cells, and then express on the cell surface. Helper T cells having recognized them are activated, and induce or enhance an immunoreaction against tumors by producing various cytokines which activate other immunocompetent cells.

Accordingly, if an immunotherapy that targets antigens specifically and highly expressed in these cancers is developed, such a therapy may effectively eliminate only cancers without causing any harmful event on one's own normal organs. It is also expected that the therapy can be used for any terminal cancer patients to whom other treatments should not be applied. In addition, by administering a cancer-specific antigen and peptide as a vaccine in advance to persons with a high risk of developing such cancers, cancer development may be prevented.

Although there are various therapies for pancreatic cancer, the prognosis of the cancer is very poor as compared to other cancers. This is because pancreatic cancer is difficult to detect early, progresses rapidly, and is thus often detected only at well-advanced stages. Although surgical removal is the most promising radical cure at present, respectable cases are only about 20% of the total number. Pancreas surgery is also highly invasive, and advanced cases show poor prognosis even after surgical resection. Non-removable cases are treated by chemotherapy that mainly uses gemcitabine, and radiotherapy. However, many cases show resistance to the treatment and have little cytoreductive effects, which is one of the reasons why pancreas cancer is intractable. Accordingly, if an immunotherapy targeting an antigen that is specifically and highly expressed in pancreatic cancer is developed, such a therapy may effectively eliminate only the cancer without causing any harmful events on one's own normal organs. It is also expected to become a therapy that can be applied for any patient with terminal cancer. In addition, since pancreatic cancer often recurs early after resection, the therapy is also expected to be useful as a postoperative adjunctive therapy.

The present inventors previously conducted genome-wide gene expression analysis of 27,648 human genes by cDNA microarray analysis to examine their expression profiles in 16 pancreatic cancer cases, fetal organs, and various adult normal organs. As a result, they discovered that P-cadherin (CDH3) was highly expressed in many pancreatic cancers, while it was hardly expressed in adult normal organs. Further, CDH3 was observed to be also highly expressed in most cases of cholangiocellular carcinoma, gastric cancer, colon cancer, non-small cell lung cancer, testicular cancer, cervical cancer, osteosarcoma, soft tissue sarcoma, and the like. This fact suggests that CDH3 can be a cancer-specific antigen in many cancers.

HLA-A2 is frequently observed in human populations regardless of the race, and about 30% of the Japanese carry HLA-A2. Therefore, if a peptide presented to killer T cells by HLA-A2 can be identified, it can be widely applied to not only Japanese but also western Caucasians and the like. Accordingly, the identification of cancer antigen peptides presented to killer T cells by HLA-A2 is an important task. It may be highly beneficial to apply such cancer antigen peptides to immunotherapy for lung cancer, whose morbidity and mortality rates are high all over the world.

Prior art document information relevant to the invention of the present application is shown below.

[Non-patent Document 1] Nakamura, T., et al., Oncogene 23: 2385-2400 (2004)
[Non-patent Document 2] Obama, K., et al., Hepatology 41: 1339-1348 (2005)
[Non-patent Document 3] Taniuchi, K., et al., Cancer Res 65: 3092-3099 (2005)
[Non-patent Document 4] Soler, A. P., et al., Cancer 86: 1263-1272 (1999)
[Non-patent Document 5] Paredes, J., et al., Clin Cancer Res 11: 5869-5877 (2005)
[Non-patent Document 6] Ingunn, M., et al., J Clin Oncol 22: 1242-1252 (2004)
[Non-patent Document 7] Glenn, L., et al., J Cell Biol 139: 1025-1032 (1997)
[Non-patent Document 8] Bauer, R., et al., Exp. Mol. Pathol. 81: 224-230 (2006)
[Non-patent Document 9] Muzon-Guerra, M. F., et al. Cancer 103: 960-969 (2005)
[Non-patent Document 10] Marck, V. V., et al., Cancer Res. 65: 8774-8783 (2005)

DISCLOSURE OF THE INVENTION

[Problems to be Solved by the Invention]

An objective to be achieved by the present invention is to develop means to realize an immunotherapy that suppresses cancer growth by improving the immunity of cancer patients against cancer, as a novel therapy for metastatic or intractable cancers which are difficult to be treated by surgical treatments, chemotherapy, and radiotherapy, which are used to treat pancreatic cancer, cholangiocellular carcinoma, gastric cancer, colon cancer, non-small cell lung cancer, and the like. The present invention provides identified peptides that are derived from proteins specifically and highly expressed in cancers and are presented to killer T cells by HLA-A2. This enables an immunotherapy that can be applied to about 30% of Japanese patients with various cancers that highly express CDH3.

[Means for Solving the Problems]

The present inventors identified CDH3 (GenBank Accession No. NM_001793) as a gene highly expressed in pancreatic cancer, by cDNA microarray analysis of pancreatic cancer tissues. In order to examine whether or not antitumor immunity is induced by CDH3 specific killer T cells, HLA-A2 transgenic mice expressing HLA-A2, which is carried by about 30% of the Japanese, were used. Specifically, HLA-A2 transgenic mice were immunized with mouse bone marrow-derived dendritic cells pulsed with a human CDH3 peptide having an HLA-A2 binding motif to examine whether HLA-A2 restricted peptide-specific killer T cells would be induced. The ELISPOT method was used to detect γ-interferon (IFN-γ) produced by killer T cells that had been activated by recognizing the peptide presented by HLA-A2, and thereby examine whether killer T cells specific to the CDH3 peptide were induced or not in spleen cells of the immunized mice. As a result, the present inventors identified two novel CDH3 peptides applicable to immunotherapy for HLA-A2 positive cancer patients. In addition, it was revealed that CDH3 responsive CTLs induced by using these peptides had cytotoxicity specific to cancer cells expressing endogenous CDH3 and HLA-A2 molecules, and that the CTLs recognized the target cells in an HLA-class I-restricted manner. Moreover, it was also revealed that the growth of tumors transplanted to NOD/SCID mice was significantly suppressed by intravenously injecting CD8 positive cells induced by the peptides (CTL adoptive immunity method).

More specifically, the present invention provides:
(1) a peptide of the following (A) or (B):
(A) a peptide including an amino acid sequence of SEQ ID NO: 1 or 2,
(B) a peptide including an amino acid sequence of SEQ ID NO: 1 or 2, wherein one, two, or several amino acid(s) are substituted, deleted, inserted, and/or added, and wherein the peptide has an activity to induce a cytotoxic (killer) T cell;
(2) the peptide of (1), wherein the second amino acid from the N-terminus is leucine or methionine;
(3) the peptide of (1), wherein the C-terminal amino acid is valine or leucine;

(4) an agent for inducing immunity against cancer, including one or more peptide(s) of (1) as an active ingredient;
(5) an agent for treating and/or preventing cancer, including one or more peptide(s) of (1) as an active ingredient;
(6) an agent for inducing an antigen presenting cell having cytotoxic (killer) T cell-inducing activity, including one or more peptide(s) of (1) as an active ingredient;
(7) an agent for inducing an antigen presenting cell having cytotoxic (killer) T cell-inducing activity, including one or more polynucleotide(s) encoding the peptide of (1) as an active ingredient;
(8) an agent for inducing a cytotoxic (killer) T cell, including one or more peptide(s) of (1) as an active ingredient;
(9) an antibody against the peptide of (1);
(10) a helper T cell, a cytotoxic (killer) T cell, or a group of immunocytes including these cells, which is induced by using the peptide of (1);
(11) an antigen presenting cell that presents a complex including the peptide of (1) and an HLA antigen;
(12) the antigen presenting cell of (11), which is induced by the agent of (6) or (7);
(13) an exosome that presents a complex including the peptide of (1) and an HLA antigen;
(14) the exosome of (13), wherein the HLA antigen is HLA-A2 (HLA-A2*0201);
(15) a method for inducing an antigen presenting cell having cytotoxic (killer) T cell-inducing activity, including a step of contacting the antigen presenting cell with the peptide of (1);
(16) a method for inducing an antigen presenting cell having cytotoxic (killer) T cell-inducing activity, including a step of transfecting a polynucleotide encoding the peptide of (1) into an antigen presenting cell;
(17) a method for inducing a cytotoxic (killer) T cell, including a step of contacting a T cell with the peptide of (1);
(18) a method for inducing immunity against cancer, including a step of administering the peptide of (1) to a subject;
(19) a method for treating and/or preventing cancer, including a step of administering the peptide of (1) to a subject;
(20) use of the peptide of (1) for manufacture of an agent for inducing immunity against cancer; and
(21) use of the peptide of (1) for manufacture of a medicament for treating and/or preventing cancer.

MODE FOR CARRYING OUT THE INVENTION

Figure 1:
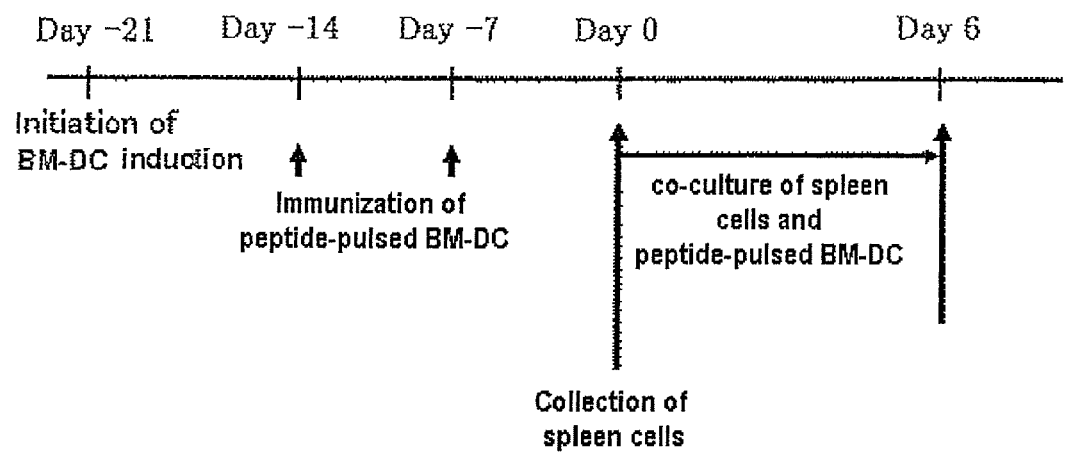
FIG. 1 shows the protocol for identifying CDH3 peptides recognized by HLA-A2 restricted killer T cells. (The day on which the spleen cells were isolated from immunized mice is set as "Day 0").

The terms "a", "an", and "the" as used herein mean "at least one" unless otherwise specifically indicated.

Unless otherwise defined, all technical and the scientific terms used herein have the same meaning commonly understood by those of ordinary skill in the art to which the present invention belongs.

The peptide according to the present invention is an epitope restricted by HLA-A2 which is an HLA allele generally found in Japanese and Caucasian populations. Specifically, candidates of HLA-A2 binding peptides derived from CDH3 were selected using as an index their binding affinity to HLA-A2. The selected peptides were evaluated by testing whether killer T cells would be induced in the body of HLA-A2 transgenic mouse by dendritic cells derived from the HLA-A2 transgenic mouse bone marrow cells (BM-DCs) pulsed with a selected peptide. Killer T cells were induced by CDH3-4 (FILPVLGAV (SEQ ID NO: 1)) and CDH3-7 (FIIENLKAA (SEQ ID NO: 2)), in the body of the HLA-A2 transgenic mouse. The killer T cells induced by these peptides showed an immune response to BM-DCs to which these peptides were added. However, these killer T cells did not show any immune response to BM-DC to which the peptides were not added. These results demonstrate that the peptides derived from CDH3 are useful as peptides for inducing an immune reaction against CDH3 presenting cells, and that the peptides derived from CDH3 are HLA-A2 restricted epitope peptides. CDH3 was highly expressed in most cases with cancers such as pancreatic cancer, cholangiocellular carcinoma, gastric cancer, colon cancer, non-small cell lung cancer, testicular cancer, cervical cancer, osteosarcoma, and soft tissue tumors. This indicates that CDH3 is useful as a target for immunotherapy in many cancers.

(1) Peptides According to the Present Invention and Agents for Inducing Immunity Against Cancer Containing these Peptides A peptide according to the present invention is any one of the following peptides:

(A) a peptide including an amino acid sequence of SEQ ID NO: 1 or 2;

(B) a peptide including an amino acid sequence of SEQ ID NO: 1 or 2, wherein one, two, or several amino acid(s) are substituted, deleted, inserted, and/or added, and wherein the peptide has an activity to induce killer T cells;

(C) the peptide of (B), in which the second amino acid from the N-terminus is leucine or methionine; and (D) the peptide of (B), in which the C-terminal amino acid is valine or leucine.

A peptide according to the present invention is an epitope peptide having less than 40 amino acids, preferably less than 20 amino acids, more preferably less than 15 amino acids, which includes the amino acid sequence of SEQ ID NO: 1 or 2, and has the activity to induce killer T cells. Alternatively, the epitope peptide may include a peptide including an amino acid sequence of SEQ ID NO: 1 or 2, wherein one, two, or several amino acid(s) are substituted, deleted, inserted, and/or added, as long as the activity to induce killer T cells is retained. The number of residues substituted, deleted, inserted, and/or added is generally 5 amino acids or less, preferably 4 amino acids or less, more preferably 3 amino acids or less, even more preferably 1 amino acid or 2 amino acids.

Variant peptides (i.e., peptides including amino acid sequences obtained by altering the original amino acid sequences by substitution, deletion, insertion, and/or addition of one, two, or several amino acid residues) are known to retain original biological activities (Mark D F et al., (1984) Proc Natl Acad Sci USA 81: 5662-6; Zoller M J and Smith M, (1982) Nucleic Acids Res 10: 6487-500; Dalbadie-McFarland G et al., (1982) Proc Natl Acad Sci USA 79: 6409-13).

Amino acid alterations preferably retain properties of the original amino acid side chains. Examples of properties of amino acid side chains are hydrophobic amino acids (A, I, L, M, F, P, W, Y, V), hydrophilic amino acids (R, D, N, C, E, Q, G, H, K, S, T), and side chains having following functional groups or characteristics in common: aliphatic side chains (G, A, V, L, I, P); hydroxy group-containing side chains (S, T, Y); sulfur atom-containing side chains (C, M); carboxylic acid- and amide-containing side chains (D, N, E, Q); base-containing side chains (R, K, H); and aromatic-containing side chains (H, F, Y, W), where characters within the parentheses refer to one letter codes of amino acids.

In a preferred embodiment, peptides of the present invention (immunogenic peptides) are nonapeptides (9-mers) or decapeptides (10-mers).

Herein, a peptide having killer T cell-inducing activity means a peptide having T cell inducing activity that stimulates killer T cells (cytotoxic T cells/CTLs).

In order to obtain peptides with high binding affinity and killer T cell-inducing activity, the amino acid sequence of a partial peptide of naturally-occurring CDH3 may be altered by substitution, deletion or addition of one, two, or several amino acids. Herein, the term "several" refers to 5 or less, preferably 3 or less, more preferably 2 or less. Further, since the regularity in the peptide sequences having high affinity to HLA antigens is known (Kubo R T, et al., (1994) J. Immunol., 152: 3913-24; Rammensee H G, et al., (1995) Immunogenetics. 41: 178-228; Kondo A, et al. (1995) J. Immunol. 155: 4307-12), the peptides of the present invention (epitope peptides) can be altered in order to improve their affinity to the HLA antigens based on the regularity. For example, peptides with high HLA-2 binding affinity can be obtained by replacing the second amino acid from the N-terminus with leucine or methionine. Similarly, peptides with high HLA-2 binding affinity can also be obtained by replacing the C-terminal amino acid with valine or leucine.

When the sequence of an epitope peptide is the same as a part of an amino acid sequence of an endogenous or exogenous protein having a different function, side effects such as autoimmune disorders or allergy symptoms against a specific substance can be caused. In order to avoid such side effects, an altered epitope peptide should not be identical with the amino acid sequences of known proteins. For this purpose, it is necessary to carry out a homology search using available databases to confirm that there is no endogenous or exogenous protein with a different function which shows 100% homology with the altered epitope peptide. By this process, risks caused by the above-mentioned amino acid sequence alteration for increasing the binding affinity with the HLA antigen and/or for increasing the killer T cell-inducing activity, can be avoided.

Although the above-described peptides having high binding affinity to HLA antigens are expected to be highly effective as cancer vaccines, candidate peptides selected using high affinity as an index must be examined to see whether they actually have killer T cell-inducing activity. The killer T cell-inducing activity can be confirmed by: inducing antigen presenting cells having the human MHC antigen (for example, B-lymphocytes, macrophages, and dendritic cells), or more specifically, inducing dendritic cells derived from human peripheral blood mononuclear leukocytes; stimulating them with a peptide of interest; then mixing them with CD8 positive cells; and measuring the cytotoxic activity against the target cell. As a reaction system, transgenic animals that express the human HLA antigen (as described in, for example, BenMohamed L, et al., (2000) Hum. Immunol. 61 (8): 764-79, Related Articles, Books, and Linkout) can be used. For example, the target cells can be radiolabeled by $^{51}$Cr or the like, and cytotoxic activity can be calculated from the radioactivity released from the target cells. Alternatively, the target cells can be examined by: measuring IFN-γ produced and released from the killer T cells in the presence of the antigen presenting cells having the immobilized peptide; and visualizing the IFN-γ production zone on the culture medium using an anti-IFN-γ monoclonal antibody.

As shown in Examples, the result of examination of the killer T cell-inducing activity of peptides showed that the peptides having high binding affinity to the HLA antigen do not necessarily have high killer T cell-inducing activity. However, the peptides containing the amino acid sequence of CDH3-4 (FILPVLGAV (SEQ ID NO: 1)) or CDH3-7 (FI-IENLKAA (SEQ ID NO: 2)) showed especially high killer T cell-inducing activity.

As described above, the present invention provides peptides having killer T cell-inducing activity, more specifically, peptides including the amino acid sequence of SEQ ID NO: 1 or 2, or variants thereof (i.e., amino acid sequences in which one, two, or several amino acids are substituted, deleted, inserted, and/or added). The amino acid sequences of peptides containing the nine amino acids of SEQ ID NO: 1 or 2, or variants thereof are preferably not identical to those of other endogenous proteins. Especially, peptides with high HLA-A2 binding affinity can be obtained by replacing the second amino acid from the N-terminus with leucine or methionine, and/or by replacing the C-terminal amino acid with valine or leucine.

The peptides of the present invention may include modifications such as glycosylation, side chain oxidation, and phosphorylation, unless the peptides lose their killer T cell-inducing activity. Other modifications include, for example, D-amino acids or other amino acid analogues which can be used to increase serum half-life of the peptides.

Methods for obtaining and manufacturing the peptides of the present invention are not particularly limited. They may be chemically-synthesized peptides or recombinant peptides produced by gene-recombination technology.

Chemically-synthesized peptides of the present invention can be synthesized in accordance with chemical synthesis methods such as the Fmoc method (fluorenylmethyloxycarbonyl method) and the t-Boc method (t-butyloxycarbonyl method). The peptides of the present invention can also be synthesized utilizing various commercially-available peptide synthesizers.

The peptides of the present invention can be manufactured as recombinant proteins by obtaining DNAs having the nucleotide sequences encoding the peptides, or variants or homologs thereof, and introducing them into a suitable expression system.

Expression vectors used may preferably be any vectors that can be autonomously duplicated in host cells, or can be incorporated into a chromosome of the host cell, and contain a promoter on a suitable locus to allow expression of a peptide-encoding gene. Transformants having a gene encoding the peptide of the present invention can be produced by introducing the above-mentioned expression vector into the host. The host may be any of bacteria, yeast, animal cells and insect cells, and introduction of the expression vector to the host can be carried out using any known techniques depending on the host.

In the present invention, the recombinant peptide of the present invention can be isolated by culturing the transformant produced as described above, producing and accumulating the peptide in the culture, and collecting the peptide from the culture.

When the transformant is a prokaryote such as *E. coli* or an eukaryote such as yeast, the culture medium for cultivating these microorganisms may either be a natural medium or a synthetic medium, as long as it contains a carbon source, nitrogen source, minerals and the like that can be utilized by the microorganisms and allows efficient culture of the transformant. The culture conditions may be those usually used for culturing the microorganisms. After culturing, the peptide of the present invention can be isolated and purified from the culture of the transformant using conventional methods for peptide isolation and purification.

Peptides including an amino acid sequence in which one, two, or several amino acids are substituted or added in the amino acid sequence of SEQ ID NO: 1 or 2 can be appropriately produced or obtained by a person skilled in the art based on the information on the nucleotide sequence encoding the amino acid sequence of SEQ ID NO: 1 or 2. Specifically, the gene encoding a peptide which contains an amino acid sequence in which one, two or several amino acids are substituted, deleted, inserted, and/or added in the amino acid sequence of SEQ ID NO: 1 or 2 and has killer T cell-inducing activity can also be produced by any method known to a person skilled in the art, such as chemical synthesis, genetic engineering techniques or mutagenesis. For example, the site-directed mutagenesis method, one of the genetic engineering techniques, is useful because it can introduce a specific mutation into a specific position. It can be carried out according to the methods described in Molecular Cloning: A laboratory Manual, 2nd Ed., Cold Spring Harbor Laboratory, Cold Spring Harbor, N.Y., 1989 (abbreviated hereinafter as Molecular Cloning 2nd Ed.), Current Protocols in Molecular Biology, Supplement 1-38, John Wiley & Sons (1987-1997) (abbreviated hereinafter as Current Protocols in Molecular Biology), and the like.

The above-described peptides of the present invention can induce immunity against cancer, as also shown below in the Examples. Therefore, according to the present invention, agents for inducing immunity against cancer containing the peptides of the present invention are provided. The agents for inducing immunity of the present invention can also be prepared as a mixed formulation by combining two or more epitope peptides. Agents for inducing immunity formulated by combining multiple kinds of peptides may be a cocktail, or may be mutually linked using standard techniques. The epitope peptides to be combined may be peptides having different amino acid sequences derived from the same gene, or may be peptides having amino acid sequences derived from different genes. When the peptides of the present invention are administered to a subject, the administered peptides are densely-presented on HLA antigens of antigen presenting cells, and subsequently, killer T cells, which react specifically with the complexes formed between the administered peptides and the HLA antigens, are induced. Alternatively, by contacting dendritic cells collected from a subject with the peptides of the present invention (or by pulsing with the peptides of the present invention dendritic cells collected from a subject), the antigen presenting cells that present the peptides of the present invention on their cell surface can be obtained. By administrating these antigen presenting cells back to each subject, killer T cells are induced in the subject's body, and as a result, immunity responses to target cells presenting the peptides of the present invention can be enhanced.

When used in vitro or in vivo, preferably in vitro, the agents for inducing immunity against cancer according to the present invention can induce helper T cells, killer T cells, or groups of immunocytes including these cells, thereby conferring immunity against cancer.

(2) Pharmaceutical Agents for Treating and/or Preventing Cancer According to the Present Invention (Cancer Vaccines)

It was shown in the Examples that the peptides of the present invention can induce cancer cell-specific killer T cells in vivo. Moreover, it was shown in the previous invention that CDH3 was highly expressed in most cases such as pancreatic cancer, cholangiocellular carcinoma, gastric cancer, colon cancer, non-small cell lung cancer, testicular cancer, cervical cancer, osteosarcoma, soft tissue sarcoma, or such. Accordingly, the agents for inducing immunity including the peptides of the present invention are expected to be effective as agents for treating and/or preventing cancer. That is, by injecting the peptides of the present invention, together with a suitable adjuvant into the body, or after pulsing with the peptides the antigen presenting cells such as dendritic cells, tumor-attacking killer T cells are induced and activated, and as the result, antitumor effects can be expected. Further, genes encoding the peptides of the present invention can be incorporated into suitable vectors. Human antigen presenting cells (dendritic cells, etc.) and bacteria such as BCG *Mycobacterium tuberculosis* that are transformed by the recombinant DNA, or viruses such as vaccinia virus that have a genome-integrated DNA encoding the peptide of the present invention, can be effectively used as live vaccines for treating and/or preventing human cancer. The dosages and the administration methods for the cancer vaccines are the same as those for usual smallpox vaccines or BCG vaccines.

In relation to the present invention, the term "vaccine" (also called immunogenic composition) refers to a substance that induces antitumor immunity or suppresses various cancers when inoculated to an animal. According to the present invention, it was suggested that the peptide including the amino acid sequence of SEQ ID NO: 1 or 2 is an HLA-A2 restricted epitope peptide that can induce strong and specific immune responses against CDH3 presenting cells. Accordingly, the present invention also includes methods for inducing antitumor immunity by using the peptides including the amino acid sequence of SEQ ID NO: 1 or 2, or variants thereof that include substitutions, deletions, or additions of one, two, or more amino acids. In general, antitumor immunity includes the following immune responses:

(1) induction of killer T cells against tumors containing CDH3 expressing cells;
(2) induction of antibodies that recognize tumors containing CDH3 expressing cells; and
(3) induction of anticancer cytokine production.

When a particular peptide induces any one of these immune responses through inoculation to an animal, that peptide is determined to have an antitumor immunity-inducing effect. Induction of antitumor immunity by the peptide can be detected by observing the in vivo or in vitro response of the immune system to the peptide in a host.

For example, methods for detecting induction of killer T cells are well known. A foreign substance that invades a living body is presented to T cells and B cells by the action of antigen presenting cells (APC). T cells that respond to antigens presented by antigen presenting cells in an antigen-specific manner differentiate into killer T cells (also called cytotoxic T lymphocytes or CTLs) through stimulation by antigens, and then proliferate. Herein, this process is called "activation" of T cells. Killer T cell induction by a specific peptide can be evaluated by presenting the peptide on T cells using peptide-pulsed antigen-presenting cells, and then detecting the induction of killer T cells. Furthermore, antigen presenting cells have effects of activating $CD4^+$ T cells, $CD8^+$ T cells, macrophages, eosinophils, and NK cells. Since $CD4^+$ T cells are important in antitumor immunity, antitumor immunity-inducing effect of the peptide can be evaluated using the activating effects of these cells as indicators.

Methods for evaluating killer T cell-inducing effects, wherein the killer T cells are induced using dendritic cells (DCs) as antigen presenting cells are well known in the art. Among antigen presenting cells, DCs have the strongest killer T cell-inducing effect. This method involves, first contacting a test peptide with DCs, and then contacting the DCs with T cells. T cells having cytotoxic effects on target cells are detected from the T cells contacted with DCs. If the T cells show cytotoxic activity against the target cells, it means that the test peptide has an activity to induce cytotoxic T cells. Activity of killer T cells against target cells such as tumor cells can be detected, for example, using lysis of $^{51}Cr$-labeled tumor cells as an indicator. Alternatively, the degree of tumor cell damage can be evaluated using $^3H$-thymidine uptake activity or release of lactose dehydrogenase (LDH) as an index.

Test peptides confirmed by these methods to have killer T cell-inducing activity are peptides having DC-activating effects and subsequent killer T cell-inducing activity. Therefore, peptides that induce killer T cells against tumor cells will be useful as vaccines against cancers presenting CDH3. Furthermore, antigen presenting cells that have acquired an ability to induce killer T cells against cancers through contact with the peptide will be useful as vaccines against cancer. Additionally, killer T cells that have acquired cytotoxicity by presentation of peptides by antigen presenting cells can also be used as vaccines against cancers presenting CDH3. The method for treating cancer using antitumor immunity by antigen presenting cells and killer T cells is called cytoimmunotherapy.

In general, when using peptides for cytoimmunotherapy, efficiency of killer T cell induction can be enhanced by combining a plurality of peptides having different structures. Therefore, when stimulating DCs with protein fragments, it is advantageous to use a mixture of more than one type of peptide fragments.

Induction of antitumor immunity by peptides can also be evaluated by observing the induction of antibody production against tumors. For example, when antibodies against peptides are induced in laboratory animals immunized with the peptides, and when growth, proliferation, and/or metastasis of tumor cells are suppressed by these antibodies, it is determined that the peptides induce antitumor immunity.

Antitumor immunity can be induced by administering a vaccine of the present invention, and induction of antitumor immunity enables treatment and prevention of cancer. Effects of treating cancer or preventing cancer incidence may include inhibition of cancer cell growth, regression of cancer cells, and suppression of cancer cell development. Decrease in mortality rate of individuals who have cancer, decrease in tumor markers in blood, and reduction of detectable symptoms accompanying cancer are also included in the effects of treatment or prevention of cancer. Such therapeutic or preventive effects of the vaccine against cancer are preferably statistically significant compared to that of a control without vaccine administration. For example, the effects are observed at a significance level of 5% or less. Statistical methods that may be used for determining the statistical significance are, for example, Student t-test, Mann-Whitney U test, or ANOVA.

In the present invention, the subject is preferably a mammal. Examples include humans, non-human primates, mice, rats, dogs, cats, horses, or cattle, but are not limited thereto.

Peptides of the present invention can be administered to a subject in vivo or ex vivo. Furthermore, to produce an immunogenic composition for treating or preventing cancer, an immunogenic peptide of the present invention, that is, the amino acid sequence of SEQ ID NO: 1 or 2, or nonapeptides selected from variant peptides thereof, may be used.

More specifically, the present invention provides pharmaceutical agents for treating tumor or for preventing growth, metastasis, and such of tumors, including one or more peptides of the present invention as active ingredients. Peptides of the present invention are particularly useful for treating pancreatic cancer, cholangiocellular carcinoma, gastric cancer, colon cancer, non-small cell lung cancer, testicular cancer, cervical cancer, and tumors such as osteosarcoma and soft tissue sarcoma.

Peptides of the present invention can be administered directly to a subject as a pharmaceutical agent formulated by ordinary formulation methods. Such formulation may include, in addition to the peptides of the present invention, pharmaceutically acceptable carriers, excipients, and such as necessary. Pharmaceutical agents of the present invention may be used for treating and preventing various tumors.

Furthermore, to effectively establish cellular immunity, adjuvants can be mixed into pharmaceutical agents for treating and/or preventing tumors including one or more peptides of the present invention as active ingredients. Alternatively, this composition may be co-administered with other active ingredients such as antitumor agents. Appropriate formulations also include granules. Appropriate adjuvants are described in the literature (Johnson A G, (1994) Clin. Microbiol. Rev., 7: 277-89). Examples of adjuvants include incomplete Freund's adjuvant, BCG, trehalose dimycolate (TDM), lipopolysaccharide (LPS), alum adjuvant, silica adjuvant, aluminum phosphate, alum hydroxide, and aluminum potassium sulfate, but are not limited thereto. Furthermore, liposomal formulations, granular formulations in which a drug is attached to beads having a diameter of several μm, and formulations in which lipids are bound to the aforementioned peptides may be used conveniently. Methods of administration may be oral administration, intradermal injection, subcutaneous injection, intravenous injection, or such, and may include systemic administration or local administration near the target tumor.

The dose of the peptides of the present invention can be adjusted appropriately according to the disease to be treated, age and body weight of the patient, method of administration, and such. The dose is usually 0.001 mg to 1,000 mg, preferably 0.01 mg to 100 mg, and more preferably 0.1 mg to 10 mg. Preferably this is administered once in a few days to once in a few months, but those skilled in the art can easily select appropriate doses and methods of administration, and selection and optimization of these parameters are fully within the scope of conventional technique. The form of the formulation is also not particularly limited, and they may be freeze-dried, or granulated by adding excipients such as sugar.

Adjuvants for increasing the tumor-responsive T cell-inducing activity that can be added to the pharmaceutical agents of the present invention include bacterial components of BCG bacteria and such including muramyl dipeptide (MDP), ISCOM referred to in Nature, vol. 344, p. 873 (1990), QS-21 of saponin series described in, J. Immunol. vol. 148, p. 1438 (1992) liposome, and aluminum hydroxide. Furthermore, immunostimulants such as lentinan, sizofuran, and Picibanil can also be used as adjuvants. Cytokines and such that enhance the proliferation and differentiation of T cells, such as IL-2, IL-4, IL-12, IL-1, IL-6, and TNF, as well as CpG and lipopolysaccharides (LPS) that activate the natural immune system by binding to Toll-like receptors and α-galactosylceramide which activate NKT cells can also be used as adjuvants.

Vaccine compositions of the present invention include a component which primes killer T cells. Lipids have been identified as substances that prime against viral antigens in vivo. For example, palmitic acid residues can be attached to the ε-amino group and α-amino group of a lysine residue, and then linked to an immunogenic peptide of the present invention. The lipidated peptide can then be administered directly by any one of incorporation into a micelle or particle, encapsulation into a liposome, or emulsification in an adjuvant. Another possible example of lipid priming is priming with an *Escherichia coli* (*E. coli*) lipoprotein such as tripalmitoyl-S-glycerylcysteinyl-seryl-serine (P3CSS) when a covalent bond is formed with a suitable peptide (Deres K., et al., (1989) Nature 342: 561-4).

Immunogenic peptides of the present invention can also be expressed by viral vectors or bacterial vectors. Examples of appropriate expression vectors include attenuated virulence viral hosts such as vaccinia or fowlpox. For example, vaccinia virus can be used as a vector to express a nucleotide sequence encoding the peptide. By introducing the recombinant vaccinia virus into host cells, immunogenic peptides are expressed, and this elicits an immune response. Immunization method using vaccinia vectors is described, for example, in U.S. Pat. No. 4,722,848. Bacille de Calmette et Guerin (BCG) may also be used. BCG vectors are described in Stover C K, et al., (1991) Nature 31: 456-60. A wide variety of other vectors useful for therapeutic administration or immunization including adeno and adeno-associated virus vectors, retroviral vectors, *typhoid bacillus* (*Salmonella typhi*) vector, and detoxified anthrax toxin vectors are known in the art. See for example, Shata M T, et al., (2000) Mol. Med. Today 6: 66-71; Shedlock D J and Weiner D B et al., (2000) J. Leukoc. Biol. 68: 793-806; and Hipp J D, et al., (2000) In Vivo 14: 571-85.

Furthermore, to effectively induce killer T cells in the body of a patient, the antigenic peptide is added in vitro to present antigen to cells collected from a patient or to cells of another person sharing a part of an HLA allele (allo), and then the cells are administered to the patient intravascularly or locally to the tumor. Alternatively, after induction of killer T cells in vivo by adding the peptide to the patient's peripheral blood lymphocytes and culturing it in vivo, the cells can be administered to the patient intravascularly or locally to the tumor. Such treatment by cell transfer has already been carried out as cancer therapy and is a well known method among those skilled in the art.

Types of cancers in the present invention are not particularly limited, and specific examples include esophageal cancer, breast cancer, thyroid cancer, colon cancer, pancreatic cancer, malignant melanoma, malignant lymphoma, osteosarcoma, pheochromocytoma, head and neck cancer, uterine cancer, ovarian cancer, brain tumor, chronic myeloid leukemia, acute myeloid leukemia, kidney cancer, prostate cancer, lung cancer, gastric cancer, liver cancer, gallbladder cancer, testicular cancer, thyroid cancer, bladder cancer, and sarcoma. Examples of cancers for which application of the present invention is suitable are preferably pancreatic cancer, cholangiocellular carcinoma, gastric cancer, colon cancer, or lung cancer.

(3) The Antibodies of the Present Invention

The present invention is directed to antibodies which recognize a part of or whole peptide of the present invention mentioned above as an epitope (antigen) and is also directed to killer T cells that are induced by in vitro stimulation using the proteins or the peptides. In general, killer T cells demonstrate more potent antitumor activity than the antibodies.

Furthermore, similarly to the peptides of the present invention, the antibodies of the present invention are useful as an agent for preventing and/or treating cancers expressing CDH3 as long as they can inhibit the activity of the cancer antigen CDH3. In one practical use, the peptides or the antibodies of the present invention may be administered as is or with a pharmaceutically acceptable carrier and/or diluent, with an adjuvant if needed, by injection or by transdermal absorption through mucous membranes by spraying or such method. More specifically, human serum albumin can be exemplified as a carrier mentioned herein, and PBS, distilled water and such can be exemplified as a diluent.

The antibodies of the present invention can be polyclonal antibodies or monoclonal antibodies, and can be produced by methods known to those skilled in the art.

For example, polyclonal antibodies can be obtained by immunizing mammals or avian species with a peptide of the present invention as an antigen, collecting blood from the mammals or the avian species, and separating and purifying antibodies from the collected blood. For example, mammals such as mouse, hamster, guinea pig, chicken, rat, rabbit, dog, goat, sheep, and cattle, or avian species can be immunized. Methods of immunization are known to those skilled in the art, and the antigen can be administered, for example, two or three times at 7- to 30-day intervals. The dose can be, for example, approximately 0.05 mg to 2 mg of antigen per administration. The route of administration can be suitably selected from subcutaneous, intradermal, intraperitoneal, intravenous, intramuscular administrations and such, but is not limited to any one of them. Furthermore, the antigen can be used after dissolving it in a suitable buffer, for example, a buffer containing a conventional adjuvant such as Freund's complete adjuvant or aluminum hydroxide.

Immunized mammals or avian species are reared for a certain period of time and, when the antibody titer has increased, they can additionally be immunized with, for example, 100 μg to 1,000 μg of the antigen. Blood is collected from the immunized mammals or avian species one to two months after the last administration and the blood can be separated and purified by conventional methods such as centrifugation, precipitation using ammonium sulfate or polyethylene glycol, and chromatography such as gel filtration chromatography, ion exchange chromatography, and affinity chromatography to obtain the polyclonal antibodies that recognize the peptides of the present invention as a polyclonal antiserum.

Monoclonal antibodies can be obtained by preparing hybridomas. For example, hybridomas can be obtained by cell fusion of antibody-producing cells with myeloma cell lines. Hybridomas producing monoclonal antibodies of the present invention can be obtained by cell fusion methods such as those indicated below.

Spleen cells, lymph node cells, B lymphocytes, and such from the immunized animals are used as antibody-producing cells. The peptides of the present invention are used as an antigen. Animals such as mouse and rat can be used as immunized animals, and administration of antigens to these animals can be carried out by conventional methods. For example, animals are immunized by administering several times intravenously, subcutaneously, intradermally, intraperitoneally and such with a suspension or emulsion of a peptide of the present invention, which is an antigen, and of an adjuvant such as Freund's complete adjuvant or Freund's incomplete adjuvant. Antibody-producing cells such as spleen cells are obtained from immunized animals and can be fused with myeloma cells by known methods (G. Kohler et al., Nature, 256: 495 (1975)) to generate hybridomas.

P3X63Ag8, P3U1, Sp2/0 and such of mouse can be exemplified as myeloma cell lines used for cell fusion. A fusion-promoting agent such as polyethylene glycol and Sendai virus is used for cell fusion, and hypoxanthine/aminopterin/thymidine (HAT) medium is used for selecting hybridomas by a conventional method after cell fusion. Hybridomas obtained by cell fusion are cloned by a method such as the limiting dilution method. As needed, the cell lines producing monoclonal antibodies which specifically recognize the peptides of the present invention can be obtained by screening by an enzyme immunoassay method using the peptides of the present invention.

In addition to the above methods, immunized cells can be prepared by stimulating human lymphocytes such as EB virus-infected lymphocytes in vitro using the peptides of the present invention, cells expressing the peptides, or lysates thereof. Human antibodies which bind to the peptides of the present invention can also be obtained by fusing such immunized lymphocytes with human-derived bone marrow cells such as U266 (Japanese Patent Application Kokai Publication No. (JP-A) S63-17688 (unexamined, published Japanese patent application)).

In order to produce desired monoclonal antibodies from the hybridomas thus obtained, the hybridomas can be cultured by conventional culture methods or ascites-forming methods, and the monoclonal antibodies can be purified from the culture supernatants or ascites. Purification of monoclonal antibodies from the culture supernatants or ascites can be performed by the conventional methods. For example, ammonium sulfate fractionation, gel filtration, ion exchange chromatography, affinity chromatography and such can be used in combination as needed.

Furthermore, transgenic animals having a group of human antibody genes can also be immunized using the peptides of the present invention, cells expressing the peptides, or lysates thereof. Antibody-producing cells can be collected from immunized transgenic animals to obtain hybridomas by fusing with the above-described myeloma cell lines. Desired monoclonal antibodies can then be produced from the hybridomas (WO92-03918; WO94-02602; WO94-25585; WO94-33735; WO96-34096).

Alternatively, antibody-producing immune cells such as immunized lymphocytes can also be immortalized using oncogenes to prepare monoclonal antibodies.

Monoclonal antibodies thus obtained can also be modulated using a gene manipulation technology (Borrbaeck and Larrick, (1990) Therapeutic Monoclonal Antibodies). For example, recombinant antibodies can be prepared by cloning DNA encoding an antibody from antibody-producing cells such as hybridomas and immunized lymphocytes, inserting it into a suitable vector, and transfecting this into host cells.

The antibodies of the present invention may also be antibody fragments or modified antibodies so long as they bind to the peptides of the present invention. The antibody fragments can be Fab, F(ab')2, Fv, or a single chain Fv (scFv) in which Fv fragments derived from H and L chains are linked together with a suitable linker (Huston et al., (1998) Proc Natl Acad Sci USA 85: 5879-83). More specifically, the antibody fragments can be prepared by treating antibodies with an enzyme such as papain and pepsin (Co et al., (1994) J Immunol 152: 2968-76; Better and Horwitz, (1989) Methods Enzymol 178: 476-96; Pluckthun and Skerra, (1989) Methods Emzymol 178: 497-515; Lamoyi (1986) Methods Enzymol 121: 652-

63; Rousseaux et al., (1986) Methods Enzymol 121: 663-9; Bird and Walker, (1991) Trends Biotech 9: 132-7).

The antibodies of the present invention include modified antibodies which are obtained by linking various molecules such as polyethylene glycol (PEG). The antibodies can be modified by conventional methods of chemical modification known in the technical field.

The antibodies of the present invention include chimeric antibodies including a variable region derived from a non-human antibody and a constant region derived from a human antibody, and humanized antibodies including a complementarity-determining region (CDR) derived from a non-human antibody, a framework region (FR) derived from a human antibody, and a constant region derived from a human antibody. Such antibodies can be prepared by conventional methods known in the technical field. Humanized antibodies are obtained by substituting the CDR sequence region of a human antibody with a rodent CDR region having the desired binding activity (Verhoeyen et al., (1988) Science 239: 1534-6). Accordingly, compared to chimeric antibodies, humanized antibodies are antibodies in which a smaller region of the human antibody is substituted with a corresponding region of non-human origin.

A complete human antibody having a human variable region in addition to the human framework region and constant region can also be prepared. For example, in an in vitro method, screening can be carried out using a recombinant library of bacteriophages displaying human antibody fragments (Hoogenboom and Winter, (1992) J Mol Biol 227: 381-8). Similarly, human antibodies can be produced by introducing human immunoglobulin loci into transgenic animals whose endogenous immunoglobulin genes have been partially or completely inactivated (U.S. Pat. Nos. 6,150,584, 5,545,807, 5,545,806, 5,569,825, 5,625,126, 5,633,425, 5,661,016).

The antibodies obtained as stated above can be purified to homogeneity by conventional methods known in the technical field. For example, common protein separation and purification methods can be used. The antibodies can be separated and purified by a combination of column chromatography such as affinity chromatography, filtration, ultrafiltration, salting out, dialysis, SDS polyacrylamide gel electrophoresis, isoelectric focusing electrophoresis, and such; however, separation and purification methods are not limited to these methods (Antibodies: A Laboratory Manual, Ed Harlow and David Lane, (1988) Cold Spring Harbor Laboratory). Protein A columns and protein G columns can be used as affinity columns. Protein A column can be exemplified by HyperD, POROS and Sepharose F.F (Pharmacia).

Ion exchange chromatography, hydrophobic chromatography, gel filtration, reverse phase chromatography, adsorption chromatography, and such can be exemplified as chromatography other than affinity chromatography (Strategies for Protein Purification and Characterization: A Laboratory Course Manual. Ed Daniel R. et al.). Liquid chromatography such as HPLC and FPLC can also be used as chromatography.

The antigen binding affinity of the antibodies of the present invention may be measured using, for example, absorbance determination, enzyme-linked immunosorbent assay (ELISA), enzyme immunoassay (EIA), radioimmunoassay (RIA), and immunofluorescence assay; however, the methods are not limited to these methods. For ELISA, the antibodies of the present invention are immobilized onto a plate, the peptides of the present invention are added, and a sample containing a culture supernatant of antibody-producing cells or purified antibodies are then added. In the next step, a secondary antibody having a detectable label and recognizing the antibody whose antigen-binding affinity is to be measured, is added. After washing the plate, reagents for detecting the label on the secondary antibody is added and the absorbance or such is determined. For example, enzymes such as alkaline phosphatase can be used as a label for the secondary antibody, and enzyme substrates such as p-nitrophenyl phosphate can be used as a reagent for detection. BIAcore (Pharmacia) can also be used to evaluate the activity of the antibodies.

The antibodies of the present invention can detect peptides of the present invention contained in samples. Namely, the presence of peptides of the present invention in cancer tissues can be confirmed, for example, by exposing cancer tissue biopsy specimens to the antibodies of the present invention.

Prior to the step of treating and/or preventing cancer using the peptides of the present invention, subjects to be effectively treated can be predicted before initiating the treatment by confirming the expression of the peptides of the present invention in the cancer to be treated using the antibodies of the present invention.

Furthermore, since the antibodies of the present invention recognize CDH3 peptide fragments whose expression is increased in various cancer cells, it is expected that they are applicable not only for diagnosis, but also treatment.

(4) Helper T Cells, Killer T Cells, or Group of Immunocytes Including them

The present invention is also directed to helper T cells, killer T cells, or group of immunocytes including them induced by in vitro stimulation using peptides of the present invention. For example, tumor-reactive activated T cells are induced when peripheral blood lymphocytes or tumor infiltrating lymphocytes are stimulated in vitro using the peptides of the present invention, and these activated T cells can be effectively used for adoptive immunotherapy. Also, dendritic cells which are potent antigen presenting cells can be pulsed with the peptides of the present invention or can be genetically transformed to express them, which can then be used to stimulate T cells in vivo or in vitro to induce anti-tumor immune responses.

Preferably, helper T cells, killer T cells, or group of immunocytes including them can be induced by in vitro stimulation using the peptides of the present invention and an immunostimulant. The immunostimulant herein includes cell growth factors or cytokines.

Tumors can be suppressed and cancers can be prevented and/or treated by transfusion of helper T cells, killer T cells, or group of immunocytes including them obtained as described above into the body.

Helper T cells, killer T cells, or group of immunocytes including them, which can suppress tumors as described above, can also be prepared using peptides of the present invention. Therefore, the present invention provides cell culture media containing the peptides of the present invention. Helper T cells, killer T cells, or group of immunocytes including them, which can suppress tumors, can be prepared using such cell culture media. Furthermore, the present invention provides a cell culture kit containing a cell culture medium described above and a cell culture vessel to produce helper T cells, killer T cells, or a group of immunocytes including them.

(5) Antigen Presenting Exosomes

The present invention further provides endocytic vesicles called "exosomes" which present on their surface a complex formed between a peptide of the present invention and an HLA antigen. Exosomes can be prepared, for example, by methods described in detail in the Japanese translation of Japanese Patent Application Kohyo Publication No. (JP-A) H11-510507 (unexamined Japanese national phase publication corresponding to a non-Japanese international publication) and JP-A (Kohyo) 2000-512161. Preferably, it can be prepared using antigen presenting cells obtained from a target subject for treatment and/or prevention. Exosomes of the present invention can be injected as a cancer vaccine in a manner similar to the peptides of the present invention.

The HLA antigenic type used in the present invention should match the HLA antigenic type of the subject who needs the treatment and/or prevention. An example is HLA-A2, and preferably, HLA-A2 (HLA-A*0201). "HLA-A2" signifies a protein while "HLA-A*0201" signifies a gene corresponding to a segment of the protein (this term is used because no terms are available at present representing segments of the protein).

(6) Methods for Inducing Antigen Presenting Cells and Killer T Cells

The present invention provides methods for inducing antigen presenting cells using one or more peptides of the present invention. Antigen presenting cells can be induced by pulsing dendritic cells induced from peripheral blood monocytes with one or more peptides of the present invention to stimulate the cells. When the peptides of the present invention are administered to a subject, antigen presenting cells presenting the peptides of the present invention on their surfaces can be induced in the body of the subject. Alternatively, after contacting the antigen presenting cells with peptides of the present invention (or after pulsing antigen presenting cells with peptides of the present invention), the cells can be administered to the subject as a vaccine by using an ex vivo method. For example, ex vivo administration may include the steps of:
(1) collecting antigen presenting cells from a subject; and
(2) contacting antigen presenting cells of step (1) with peptides of the present invention (or pulsing antigen presenting cells of step (1) with peptides of the present invention).

The antigen presenting cells obtained in step (2) can be administered to a subject as a vaccine.

The present invention also provides methods for inducing antigen presenting cells having a high level of killer T cell induction activity. The methods include a step of transfecting in vitro a gene including a polynucleotide encoding one or more peptides of the present invention into antigen presenting cells. The gene to be transfected can be DNA or RNA. As a method for transfection, various methods can be suitably used, which are conventionally used in the art, such as lipofection, electroporation, and a calcium phosphate method, but not limited thereto. More specifically, transfection can be performed as described in Reeves M E, et al., (1996) Cancer Res., 56: 5672-7; Butterfield L H, et al., (1998) J. Immunol., 161: 5607-13; Boczkowski D, et al., (1996) J. Exp. Med., 184:465-72; and in the published Japanese translation of WO2000-509281. When genes are transfected into antigen presenting cells, they are transcribed and translated in the cells. Proteins thus obtained are subsequently processed along the MHC class I or class II pathways and are presented, via the antigen presenting pathway, on the surface of antigen presenting cells as partial peptides.

The present invention further provides methods for inducing killer T cells using one or more peptides of the present invention. By administering one or more peptides of the present invention to the subject, killer T cells can be induced in the body of the subject, thus enhancing the immune system which targets cancer cells presenting CDH3 in tumor tissues. Alternatively, activated killer T cells can be induced by contacting antigen presenting cells from a subject and CD8 positive cells with one or more peptides of the present invention in vitro and by further contacting peripheral-blood mononuclear leukocytes with the antigen presenting cells in vitro to stimulate the cells. In ex vivo treatment methods, the immune system which targets cancer cells presenting CDH3 in tumor tissues in the subject can be enhanced by returning the activated killer T cells into the subject. For example, the methods include the steps of:

(1) collecting antigen presenting cells from a subject;
(2) contacting antigen presenting cells of step (1) with the peptides of the present invention (or pulsing antigen presenting cells of step (1) with the peptides of the present invention);
(3) mixing and co-culturing antigen presenting cells of step (2) with $CD8^+$ T cells to induce cytotoxic T cells; and
(4) collecting $CD8^+$ T cells from the co-culture of step (3).

$CD8^+$ T cells having cytotoxic activity obtained in step (4) can be administered to a subject as a vaccine.

The present invention further provides isolated killer T cells which are induced using one or more peptides of the present invention. Preferably, killer T cells induced by the method of the present invention are derived from the subject to be treated and/or prevented. They can be administered in combination with other agents including antigen presenting cells or exosomes presenting one or more peptides of the present invention. The obtained killer T cells are specific for target cells presenting a peptide which is the same as that used for induction. The target cells are those expressing CDH3 endogenously, or those transfected with the CDH3 gene. Cells presenting the peptides of the present invention on their surfaces by stimulation with the peptides of the present invention, such as cancer cells from pancreatic cancer, cholangiocellular carcinoma, gastric cancer, colon cancer, non-small-cell lung cancer, testicular cancer, cervical cancer, osteosarcoma, and soft tissue sarcoma can be targeted for attack.

The present invention also provides antigen presenting cells which present a complex formed between HLA antigen and one or more peptides of the present invention. The antigen presenting cells expressing one or more peptides of the present invention or nucleotides encoding such peptides are preferably collected from the subject to be treated and/or prevented. The peptides of the present invention, antigen presenting cells presenting the peptides, exosomes, or activated killer T cells can be administered as a vaccine in combination with other agents.

The present inventions are further explained in Examples described below. However, they are not limited to these Examples.

All prior art references cited in the present specification are incorporated herein by references.

EXAMPLES

Example 1

Expression of CDH3 in Malignant Tumors

According to past cDNA microarray analyses, CDH3 expression was increased in various malignant tumors including gastric cancer, large intestinal cancer, and such, compared to expression in normal adjacent tissues (Table 1) (Nakamura T, et al., Oncogene 2004; 23: 2385-2400; Kitahara O, Cancer Res 2001; 61: 3544-3549., Obama K, et al., Hepatology 2005; 41: 1339-1348.).

TABLE 1

|  | n | Positive rate*(%) | Relative expression ratio (mean) |
|---|---|---|---|
| Pancreatic cancer | 16/16 | 100 | 1,900,000 |
| Testicular cancer | 10/10 | 100 | 396,000 |
| Soft tissue tumor | 21/21 | 100 | 248,000 |
| Cholangiocellular carcinoma | 19/19 | 100 | 3,600 |
| Non-small cell lung cancer | 35/37 | 95 | 73,000 |
| Colorectal cancer | 31/34 | 91 | 84,000 |
| Cervical cancer | 14/19 | 74 | 1,500 |
| Gastric cancer | 20/28 | 71 | 35,000 |
| Urinary bladder cancer | 24/34 | 71 | 30 |
| Small cell lung cancer | 3/14 | 21 | 7 |
| Breast cancer | 5/81 | 6 | 1 |
| Prostate cancer | 2/57 | 4 | 1,500 |
| Renal cell carcinoma | 0/20 | 0 | 0 |
| Esophageal cancer | 0/19 | 0 | 2 |

*"Positive" means when relative expression ratio (cancer/normal tissue) is >5.

Example 2

Selection of a CDH3 Peptide Repertoire having Binding Affinity to HLA-A2

Human CDH3 amino acid sequence was searched using the BIMAS system, and 18 peptides were selected in descending order of expected binding affinity to HLA-A2 (Table 2).

TABLE 2

| Peptides' | positions | Peptides' amino acid sequences | Binding affinity scores |
|---|---|---|---|
| CDH3-1 | 659-667 | VLGAVLALL (SEQ ID NO: 3) | 84 |
| CDH3-2 | 629-637 | QLTVIRATV (SEQ ID NO: 4) | 70 |
| CDH3-3 | 602-610 | VVLSLKKFL (SEQ ID NO: 5) | 65 |
| CDH3-4 | 655-663 | FILPVLGAV (SEQ ID NO: 1) | 49 |
| CDH3-5 | 419-427 | KLPTSTATI (SEQ ID NO: 6) | 37 |
| CDH3-6 | 564-572 | VLNITDKDL (SEQ ID NO: 7) | 36 |
| CDH3-7 | 757-765 | FIIENLKAA (SEQ ID NO: 2) | 30 |
| CDH3-8 | 187-195 | AVSENGASV (SEQ ID NO: 8) | 25 |
| CDH3-9 | 152-160 | SPPEGVFAV (SEQ ID NO: 9) | 25 |
| CDH3-10 | 228-237 | VLPGTSVMQV (SEQ ID NO: 10) | 272 |
| CDH3-11 | 500-509 | TLDREDEQFV (SEQ ID NO: 11) | 153 |
| CDH3-12 | 419-428 | KLPTSTATIV (SEQ ID NO: 12) | 100 |
| CDH3-13 | 440-449 | FVPPSKVVEV (SEQ ID NO: 13) | 64 |
| CDH3-14 | 66-75 | FSTDNDDFTV (SEQ ID NO: 14) | 50 |
| CDH3-15 | 2-11 | GLPRGPLASL (SEQ ID NO: 15) | 49 |
| CDH3-16 | 101-110 | ILRRHKRDWV (SEQ ID NO: 16) | 24 |
| CDH3-17 | 223-232 | SVLEGVLPGT (SEQ ID NO: 17) | 23 |
| CDH3-18 | 655-664 | FILPVLGAVL (SEQ ID NO: 18) | 20 |

The HLA-A2 restricted killer T cell epitopes identified in the present invention are shown using underlines.

Example 3

First, dendritic cells (DCs) were induced from bone marrow cells of HLA-A2 transgenic mice by using the method described previously (Komori H et al. Clinical Cancer Research 12: 2689-2697, 2006). Subsequently, thus-obtained BM-DCs were pulsed with CDH3 peptides (10 µM), and then were administered intraperitoneally to HLA-A2 transgenic mice at $5 \times 10^5$ cells/mouse. After the immunization by administering twice at weekly intervals, mouse spleen cells were harvested and used for detection of killer T cells. In order to exactly detect the induction of killer T cells derived from $CD8^+$ T cells, spleen cells which were prepared by eliminating $CD4^+$ T cells by using MACS beads after removal of spleen were used.

FIG. 1 depicts the protocol for determining CDH3 peptides recognized by HLA-A2 restricted killer T cells in HLA-A2 transgenic mice. The day spleen cells were harvested from immunized mice is set as "Day 0".

Day-21: (1) Induction of bone marrow-derived dendritic cells (herein below, called "BM-DCs") was initiated by the addition of GM-CSF to bone marrow cells from HLA-A2 transgenic mice.

Day-14: (2) A mixture of three kinds of CDH3 peptides were added to the induced BM-DCs. After two hours, BM-DCs were administered intraperitoneally at $5 \times 10^5$ cells/mouse.

(1) and (2) were repeated twice at weekly intervals.

Day 0: Spleen cells were harvested from immunized HLA-A2 transgenic mice and were co-cultured with BM-DCs, which were again incubated with CDH3 peptide for two hours, and cultured for six days.

Day 6: To detect killer T cells which specifically recognize CDH3 peptides, T cells producing gamma interferon (IFN-γ) were quantified by ELISPOT assay after the antigenic stimulation. CDH3 peptide-pulsed BM-DCs and unpulsed BM-DCs were used as target cells.

Figure 2:
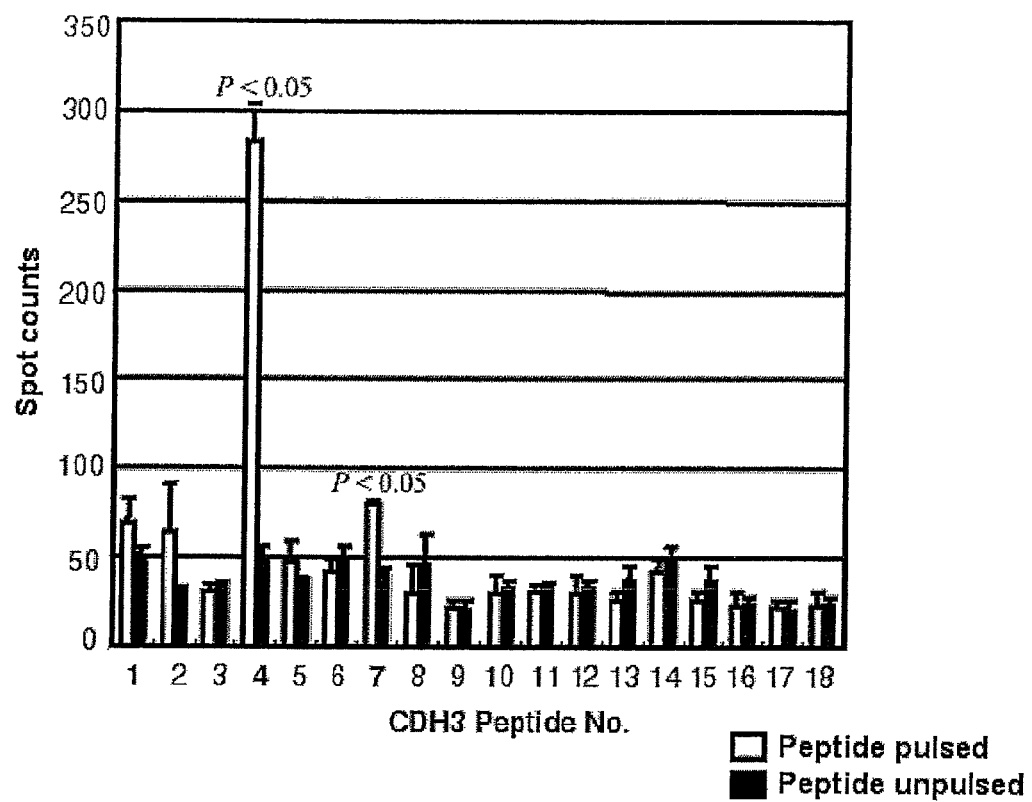
FIG. 2 depicts a graph showing the result of ELISPOT assay for 18 CDH3 peptides. ELISPOT assay was used to examine whether killer T cells obtained from immunized mice could specifically react with cells pulsed with CDH3 peptides and produce IFN-γ. Killer T cells induced with CDH3-4 or CDH3-7 peptide specifically recognized BM-DCs pulsed with CDH3 peptides and produced IFN-γ; however, killer T cells induced with other peptides did not exhibit CDH3 specific CTL immune response. Therefore, CDH3-4 and CDH3-7 peptides were confirmed to be epitope peptides capable of inducing CDH3 specific HLA-A2 restricted killer T cells. The CDH3 peptide numbers shown in FIG. 2 correspond to the peptide numbers shown in the column "Peptides' positions" in Table 2, and not to SEQ ID NOs described herein.

Investigation of Activity of CDH3 Specific Killer T Cells by ELISPOT Assay:

To confirm that killer T cells specifically reacting with CDH3 to produce IFN-γ actually exist among these cells, investigation by ELISPOT assay was conducted. IFN-γ was detected using Mouse IFN-γ ELISPOT Set (BD Biosciences). When killer T cells (effector) respond to stimulator cells (target) and produce IFN-γ, IFN-γ will be detected as red spots. BM-DCs or CDH3 peptide-pulsed BM-DCs were used as target cells. First, an ELISPOT plate (BD Biosciences) was coated with anti-mouse IFN-γ antibody for 18 hours, and then blocked by using 10% FCS/RPMI for two hours. Effector cells (100 µL/well) and target cells (100 µL/well) were mixed and cultured for 22 hours at 37° C. The experiment was conducted at the effecter/target ratio (E/T ratio) of 10:1. The plate was then washed by sterilized water, reacted with biotinylated anti-mouse IFN-γ antibody for two hours, and further reacted with streptavidin-HRP for one hour. IFN-γ positive spots were detected in substrate solution. Autoanalysis software of MINERVA TECH was used for counting the spots. As a result, CDH3 specific killer T cell immune response was observed for killer T cells induced with CDH3-4 or CDH3-7 peptide, whereas no CDH3 specific immune response was observed for killer T cells induced with other peptides (FIGS. 2 and 3).

Figure 3:
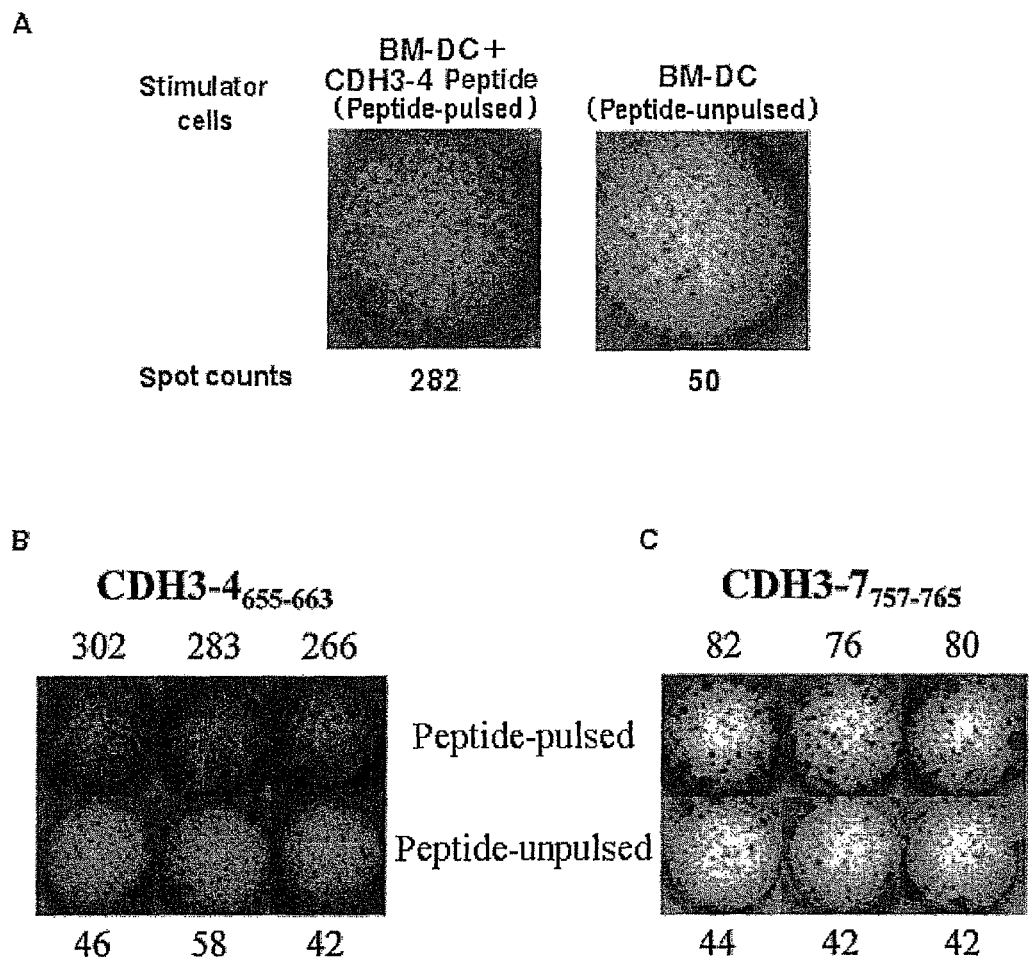
FIG. 3 depicts the photographs showing the results of ELISPOT assay detecting IFN-γ produced from killer T cells activated through specific recognition of CDH3 peptides. CD4-negative spleen cells showed 283.7±40.0 spots/well, in response to BM-DCs pulsed with $CDH3-4_{655-663}$ peptide (left in A and upper in B), whereas they showed 48.7±11.9 spots/well, in response to BM-DCs without peptide pulsing (right in A and bottom row in B) ($P<0.05$). Similarly, CD4 negative spleen cells showed 79.3±3.2 spots/well, in response to BM-DCs pulsed with $CDH3-7_{757-765}$ peptide (top row in C), whereas they showed 42.7±2.5 spots/well, in response to BM-DCs without peptide pulsing (bottom row in C) ($P<0.05$). The assay was carried out twice and gave the same results.

The results of ELISPOT assay on killer T cells induced with CDH3-4 peptide (SEQ ID NO: 1) and CDH3-7 peptide (SEQ ID NO: 2) are shown in FIG. 3.

Killer T cells showed 283.7±40.0 spots/well in response to BM-DCs pulsed with CDH3-4 peptide (SEQ ID NO: 1), whereas they showed 48.7±11.9 spots/well in the presence of BM-DCs without peptide pulsing (P<0.05). Likewise, killer T cells showed 79.3±3.2 spots/well in response to the BM-DCs pulsed with CDH3-7 peptide (SEQ ID NO: 2), whereas they showed 42.7 spots/well in the presence of BM-DCs without peptide pulsing (P<0.05).

Statistical Analysis:

Two-tailed Student's t test was used to evaluate statistical significance in the data obtained by ELISPOT assay and in tumor size between the treatment groups. A value of P<0.05 was considered to be significant. Statistical analysis was performed using a commercially available statistical software package (SPSS for Windows™, version 11.0, Chicago, Ill., USA).

Example 4

Cell Lines and HLA Expression:

Human pancreatic cancer cell line PANC1, oral cancer cell line HSC3, and TAP-deficient and HLA-A2 (A*0201) positive cell line T2 used for evaluating cytotoxic activity were purchased from Riken Cell Bank (Tsukuba, Japan). Human pancreatic cancer cell line PK8 was kindly provided by the Cell Resource Center for Biomedical Research, Institute of Development, Aging and Cancer, Tohoku University. Human colon cancer cell line HCT116 was kindly provided by Dr. B. Vogelstein, Johns Hopkins University (Baltimore, Md.). Human liver cancer cell line SKHep1 was kindly provided by Professor Kyogo Ito, Kurume University (Kurume, Japan). The expression of HLA-A2 was examined by flow cytometry using an anti-HLA-A2 monoclonal antibody (mAb) BB7.2 (One Lambda, Inc., Canoga Park, Calif., USA) in order to select HLA-A2 positive blood donors and target cell lines for cytotoxicity assays. These cells were maintained in RPMI 1640 or DMEM medium supplemented with 10% FCS in 5% $CO_2$ atmosphere at 37° C.

Lentiviral Gene Transfer:

Lentiviral vector-mediated gene transfer was performed as described previously (Tahara-Hanaoka S, et al. Exp Hematol 2002; 30: 11-17). Briefly, 17 μg of CSII-CMV-RfA and CSI-IEF-RfA self-inactivating vectors (Miyoshi H, et al. J Virol 1998; 72: 8150-8157) carrying CDH3 cDNAs and 10 μg of pCMV-VSV-G-RSV-Rev and pCAG-HIVgp were transfected into 293T cells grown in a 10-cm culture dish using Lipofectamine 2000 (Invitrogen Corporation, CA, USA). After 60 hours, the culture medium was recovered and the viral particles were pelleted by ultracentrifugation (50,000× g, two hours). The pellet was suspended in 50 μL of RPMI 1640 medium, and 10 μL of viral suspension was added to PANC1 cells or SKHep1 cells that were seeded on a flat-bottom 96-well plate at $5\times10^4$ cells per well. The expression of the transfected CDH3 was confirmed by Western blot analysis.

Induction of CDH3 Reactive Human CTLs:

PBMCs derived from heparinized blood of HLA-A2 positive pancreatic cancer patients, gastric cancer patients, colorectal cancer patients, or healthy donors were isolated by Ficoll-Conray density gradient centrifugation. Peripheral mononuclear cell (monocyte)-derived DCs were prepared by the method reported previously (Yoshitake Y, et al. Clin Cancer Res 2004; 10:6437-6448, Komori H, et al. Clin Cancer Res 2006; 12: 2689-2697). DCs were pulsed with 20 μg/mL of a candidate peptide in the presence of 4 μg/mL β2-microglobulin (Sigma-Aldrich, St. Louis, Mo., USA) for two hours at 37° C. in AIM-V (Invitrogen) containing 2% heat-inactivated autologous plasma. These DCs were then irradiated (40 Gy) and incubated with CD8 positive cells. The incubation was carried out in 24-well plates, which were prepared to contain in each well 2 mL of AIM-V supplemented with 2% autologous plasma, $1\times10^5$ peptide-pulsed DCs, $2\times10^6$ CD8$^+$ T cells, and 5 ng/mL of human recombinant IL-7 (Wako, Osaka, Japan). After two days, these cultures were supplemented with human recombinant IL-2 (PeproTec Inc.) to a final concentration of 20 IU/mL. Two additional weekly stimulations with the same peptide-pulsed autologous DCs using the same procedure were carried out on day 7 and day 14. Six days after the last stimulation, the antigen-specific responses of induced CTLs were evaluated by $^{51}$Cr release assay and IFN-γ ELISPOT assay. Various cancer cells or peptide-pulsed T2 cells ($5\times10^3$ cells/well) used as target cells were co-cultured with CTLs at a suitable effector/target ratio to conduct $^{51}$Cr release assay by a known method (Komori H, et al., Clin Cancer Res 2006; 12: 2689-2697).

CDH3-specific CTL induction from PBMCs of HLA-A2 positive healthy donors and various cancer patients by stimulation with CDH3-4$_{655-663}$ and CDH3-7$_{757-765}$ peptides were attempted. CD8 T cells sorted from PBMCs were incubated with autologous mononuclear cell (monocyte)-derived DCs pulsed with each peptide. After three stimulations, cytocidal effect against peptide-pulsed T2 cells was evaluated by $^{51}$Cr release assay (FIG. 4A) and IFN-γ ELISPOT assay. CTLs induced from PBMCs of healthy donors exhibited cytocidal effect against T2 cells pulsed with CDH3-4$_{655-663}$ peptide or CDH3-7$_{757-765}$ peptide, but not against T2 cells without peptide pulsing. Similar responses were observed regarding other donors. These results indicate that these CTLs have peptide-specific cytotoxicity.

Next, cytotoxic activity of these CTLs against human cancer cell lines expressing CDH3 and HLA-A2 was tested. As shown in FIG. 4B, CDH3 reactive CTLs stimulated with CDH3-4$_{655-663}$ peptide exhibited in healthy donors cytotoxicity to HCT116 (CDH3+, HLA-A2+), HSC3 (CDH3+, HLA-A2+), and PANC1/CDH3 (CDH3+, HLA-A2+), in which CDH3 gene was transfected into PANC1 cells; however, they did not exhibit the same effect towards PANC1 (CDH3−, HLA-A2+), SKHep1 (CDH3−, HLA-A2+), and PK8 (CDH3+, HLA-A2−). Similarly, CTLs stimulated with CDH3-7$_{757-765}$ peptide exhibited cytotoxicity towards HSC3, but not towards PANC1, PK8, and SKHep1. These cytotoxic activities were observed for CTLs derived from various cancer patients (FIG. 4C).

In order to confirm whether these peptides could be processed from the CDH3 protein under natural conditions, PANC1/CDH3 and SKHep1/CDH3 (CDH3+, HLA-A2+), in which CDH3 gene was transfected into SKHep1 cells, was used as target cells. As shown in FIG. 4C, CTLs induced by stimulation with CDH3-4$_{655-663}$ or with CDH3-7$_{757-765}$ peptide exhibited cytotoxicity against HCT116, PANC1/CDH3, and SKHep1/CDH3, but not against PANC1, SKHep1, and PK8. The above results suggest that these peptides are processed and presented on the surface of cancer cells with HLA-A2 molecules under natural conditions. CDH3 reactive CTLs had cytotoxicity specific to cancer cells that express both endogenous CDH3 and HLA-A2 molecules.

Confirmation of HLA Class I Restriction:

To confirm whether the induced CTLs could recognize target cells in an HLA-class I-restricted manner, target cancer cells were incubated with 10 μg/mL anti-HLA-class I mAb (W6/32) or with 10 μg/mL anti-HLA-DR mAb (H-DR-1) for one hour before the co-culturing of CTLs and a cancer cell line for $^{51}$Cr release assay or ELISPOT assay, and the effects of mAbs on CTLs' cytotoxic activity or IFN-γ production were examined by a known method (Gomi S, et al., Immunol 1999; 163: 4994-5004). As a result, anti-HLA-class I antibody could inhibit IFN-γ production with statistical significance in ELISPOT assay for CTLs generated by stimulation with CDH3-4$_{655-663}$ peptide against SKHep1/CDH3 (FIG. 4D, left, P<0.01). It could also inhibit cytotoxic activity against HCT116 in $^{51}$Cr release assay (FIG. 4D, middle). Similarly, anti-class I antibody could inhibit IFN-γ production with statistical significance in ELISPOT assay for CTLs generated by stimulation with CDH3-7$_{757-765}$ peptide against HSC3 cells (FIG. 4D, right, P<0.01). These results indicate that the induced CTLs recognize CDH3 expressing target cells in an HLA-class I-restricted manner.

Example 5

Adoptive Immunotherapy
In Vivo Anti-Cancer Activity of CDH3 Induced Human CTLs Used for Adoptive Immunization of NOD/SCID Mice:

In order to evaluate the therapeutic effect of CDH3 reactive CTL administration to mice that had been transplanted with CDH3 positive human cancer cells, an experimental adoptive immunotherapy was done as described previously (Komori H, et al. Clin Cancer Res 2006; 12: 2689-2697). Briefly, HCT116 cells (4×10$^6$ cells) positive for both HLA-A2 and endogenous CDH3 were inoculated to NOD/SCID mice by hypodermic injection at the right flank. When tumor size became 25 mm$^2$ on day 7 after tumor inoculation into mice, a CDH3 peptide-4$_{655-663}$ or CDH3 peptide-7$_{757-765}$-specific CTL line or, as a negative control, a CD8$^+$ T cell line stimulated with HLA-A2 restricted HIV peptide (SLYNTYATL, SEQ ID NO: 19) derived from five healthy donors and suspended in 100 μL of PBS was injected intravenously (4×10$^6$). The T cells were intravenously injected again on day 14. Sizes of tumors were measured twice a week, and evaluated by measuring two diameters perpendicular to each other using calipers. Two-tailed Student's t test was used to evaluate statistical significance in tumor sizes. A value of P<0.05 was considered to be significant. Statistical analysis was performed using a commercially available statistical software package (SPSS for Windows™, version 11.0.

Control HIV peptide-stimulated CD8+ T cells did not exhibit cytotoxicity against HCT116 cells in vitro. Tumor sizes of seven individual mice in each group (FIG. 5A) and mean±standard deviation of tumor sizes in each group (FIG. 5B) were evaluated. The control T cell line and PBS alone did not exhibit inhibitory effect on tumor growth. The tumor size in mice inoculated with the CDH3 stimulated CTLs was significantly smaller than that in mice inoculated with control HIV peptide-induced CD8+ T cells or with PBS alone (P<0.001). These results indicate the efficacy of adoptive transfer therapy of CDH3 reactive human CTLs against CDH3+ human tumor in NOD/SCID mice.

Discussion:
In the current study, the present inventors identified Cadherin 3 (CDH3)/P-cadherin as a novel TAA through cDNA microarray analysis of pancreatic cancer. CDH3 was strongly expressed in pancreatic cancer cells and faintly expressed in ovary and mammary gland based on cDNA microarray analysis. CDH3 expression was barely detectable in other vital organs. Furthermore, microarray and RT-PCR data showed that CDH3 was expressed in gastric and colorectal cancers as well as in pancreatic cancer, but hardly expressed in their normal counterpart tissues. It was already reported that CDH3 was overexpressed in the majority of pancreatic cancer tissue, whereas normal duct and acinar cells in pancreas showed almost no expression of CDH3 by immunohistochemical staining (Taniuchi K, et al. Cancer Res 2005; 65: 3092-3099). These results suggest that CDH3 could be a novel target of immunotherapy for the above cancers, which target carries a low risk of inducing an autoimmune response.

The cadherin family is classified into various subfamilies including Cadherin 1 (CDH1)/E-cadherin, Cadherin 2 (CDH2)/N-cadherin, and Cadherin 3 (CDH3)/P-cadherin, according to their tissue distribution. CDH1 is the predominant cadherin family member that is expressed in all epithelial tissues. CDH1 is assumed to act as a tumor-suppressing factor that negatively regulates invasion and metastasis of cancer cells (Frixen U H, et al. J Cell Biol 1991; 113: 173-185, Berx G, et al. Genomics 1995; 26: 281-289, Oka H, et al. Cancer Res 1993; 53: 1696-1701). CDH2 expression is increased in invasive cancers and CDH2 contributes to invasive phenomena by interacting with fibroblast growth factor (FGF) receptor and through downstream signaling (Suyama K, et al. Cancer Cell 2002; 2: 301-314). The expression and role of CDH3 in cancers is poorly understood. In a previous study, Taniuchi et al. suggested that the increased expression of CDH3 is likely to be a factor that strengthens the invasiveness of pancreatic cancer by interacting with p120ctn and Rho-family GTPase, Rac1 and Cdc42 (Taniuchi K, et al. Cancer Res 2005; 65: 3092-3099). Other previous studies suggested that CDH3 is also a factor of increased invasiveness and poor prognosis in breast cancer (Palacios J, et al. Am J Pathol 1995; 146: 605-612, Paredes J, et al. Clin Cancer Res 2005; 11: 5869-5877, Peralta Soler A, et al. Cancer 1999; 86: 1263-1272) and endometrial cancer (Stefansson I M, et al. J Clin Oncol 2004; 22: 1242-1252.).

When previous reports are taken together, objective response rate of cancer vaccines in clinical trials was low as 2.6% (Rosenberg S A, et al. Nat Med 2004; 10: 909-915). One possibility is that cancer cells escape immunity due to deletion, mutation, or down-regulation of TAAs as a consequence of immune-induction therapy. Based on the standpoint that tumor cells cannot lose antigens which are required for tumorigenesis, CDH3 would be a useful candidate TAA for anti-cancer immunotherapy.

Figure 4:
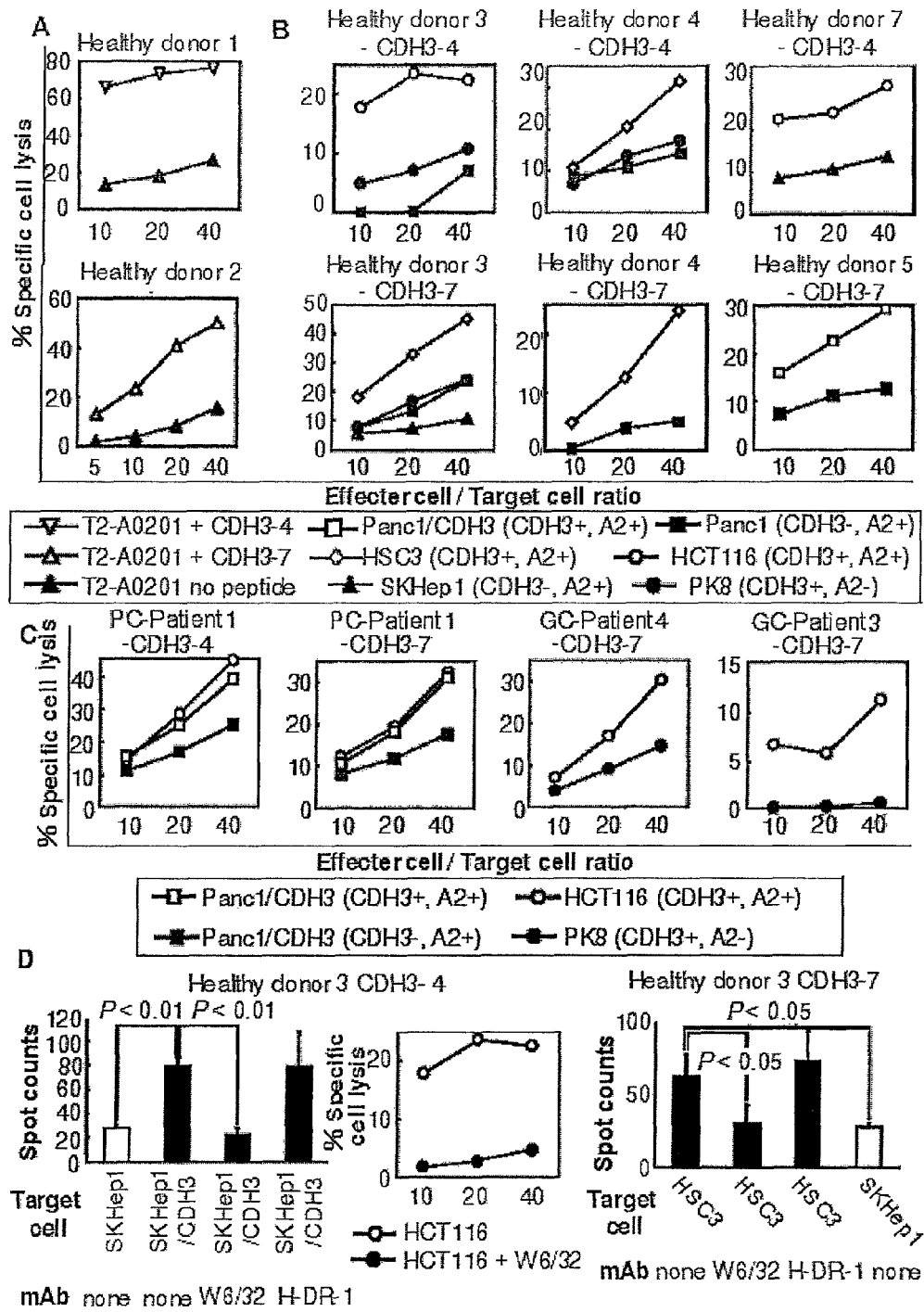
FIG. 4 depicts the line graphs showing the result of induction of CDH3-specific human CTLs from PBMCs of HLA-A2 positive healthy donors and cancer patients. A: CDH3 peptide-reactive CTLs were induced from PBMCs of HLA-A2 positive healthy donors. After stimulating three times with autologous monocyte-derived DCs pulsed with $CDH3-4_{655-663}$ (upper) or $CDH3-7_{757-765}$ (lower) peptide, cytotoxicity against T2 cells (HLA-A2 positive, TAP deficient) pulsed or unpulsed with each peptide was evaluated by standard $^{51}Cr$ release assay. The CTLs exhibited cytotoxicity to $CDH3-4_{655-663}$ (upper) or $CDH3-7_{757-765}$ (lower) peptide-pulsed T2 cells, but not to peptide-unpulsed T2 cells. B: The CTLs exhibited cytotoxicity to $CDH3^+$ $HLA-A2^+$ human colon cancer cell line HCT116, and oral squamous cancer cell line HSC3, as well as to PANC1/CDH3, which is a $CDH3^-$ $HLA-A2^+$ human pancreatic cancer cell line PANC1 transformed with the CDH3 gene. However, the CTLs did not exhibit cytotoxicity to $CDH3^-HLA-A2^+$ human liver cancer cell line SKHep1, PANC1, and $CDH3^+HLA-A2^-$ human pancreatic cancer cell line PK8. C: CDH3 reactive CTLs induced from PBMCs of HLA-A2 positive pancreatic cancer (PC) patients and gastric cancer (GC) patients exhibited cytotoxicity to HCT116 and PANC1/CDH3, but not to PANC1 and PK8. D: Inhibition of cytotoxicity by anti-HLA-class I mAb is shown. After incubating target cells, SKHep1/CDH3 and HSC3, with anti-HLA-class I mAb (W6/32, $IgG_{2a}$) or anti-HLA-DR mAb (H-DR-1, $IgG_{2a}$) for one hour, CTLs induced from PBMCs of healthy donors stimulated with $CDH3-4_{655-663}$ (left, middle) or $CDH3-7_{757-765}$ (right) peptide were added. IFN-γ production (left and right, IFN-γ ELISPOT assay) and cytotoxicity (middle, $^{51}Cr$ release assay) were markedly inhibited by W6/32, but not by H-DR-1.

In the present invention, the present inventors identified, among the 18 candidate peptides selected by the BIMAS algorithm, two HLA-A2 restricted CDH3 epitope peptides which were confirmed to induce HLA-A2 restricted mouse CTLs in HLA-A2.1 (HHD) transgenic mice. Furthermore, the present inventors confirmed that CDH3 reactive CTLs were generated from PBMCs derived from healthy donors and cancer patients by using these peptides (FIG. 4). These CTLs exhibited cytocidal effect not only towards T2 cells pulsed with its corresponding peptide but also towards cancer cell lines expressing CDH3 and HLA-A2. From the above, it is suggested that the present CDH3 peptides (CDH3-4$_{655-663}$ and CDH3-7$_{757-765}$) are naturally produced by processing from CDH3 protein in cancer cells, presented onto the cell surface together with HLA-A2 molecules, and are then recognized by CTLs.

Figure 5:
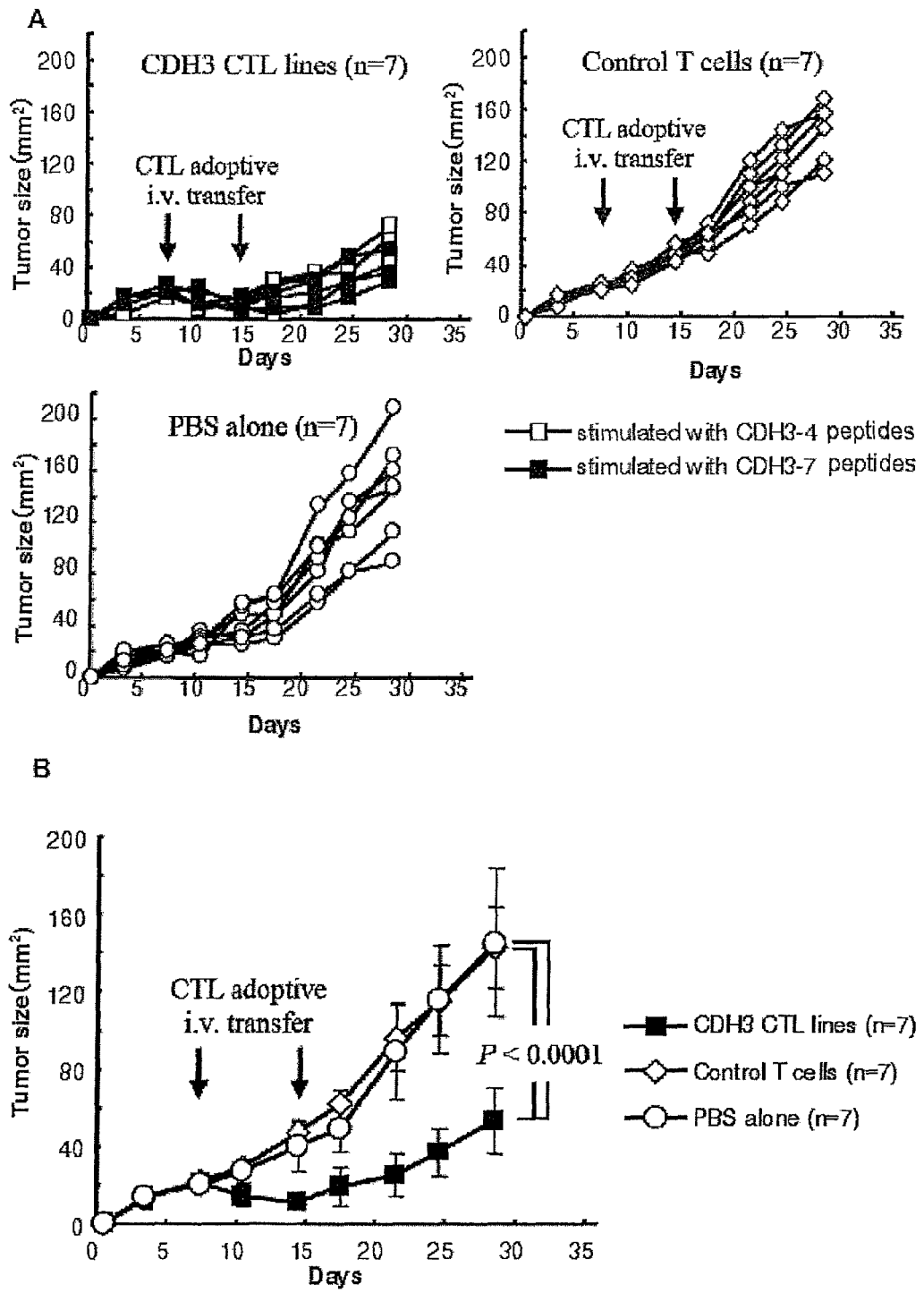
FIG. 5 depicts in vivo antitumor activity of CDH3 induced human CTLs against human cancer cells transplanted into NOD/SCID mice. A: Inhibition of growth of a human colorectal cancer cell line, HCT116 ($CDH3^+$, $HLA-A2^+$), engrafted into NOD/SCID mice after CTL transfer. When the size of the tumor reached 25 $mm^2$ on day 7 after subcutaneous tumor implantation, human CTLs reactive to $CDH3-4_{655-663}$ peptide (□) and to $CDH3-7_{757-765}$ peptide (■) were intravenously inoculated. On day 14, CTLs were inoculated again in the same manner. The control $CD8^+$ T cells stimulated with HLA-A2 restricted HIV peptide did not show cytotoxicity (◇). Tumor volumes in NOD/SCID mice that were given two administrations of CDH3 reactive CTLs (n=7), control $CD8^+$ T cells (n=7), or PBS alone (○, n=7) on day 7 and day 14 are shown. Tumor sizes are expressed in square millimeters. B: Tumor size in each group is shown with ±SD (n=7).

The cytotoxicity of the present invention's CDH3 reactive CTLs was confirmed not only in vitro by $^{51}$Cr release assay but also in vivo by CTL adoptive immunotherapy. As shown in FIG. 5, intravenous injection of CD8+ cells induced by the present invention's peptides significantly inhibited the growth of tumors engrafted into NOD/SCID mice, in comparison to the control CD8+ cells and such.

HLA-A2 (A*0201) is one of the most common HLA-alleles in various ethnic groups including Asians, Africans, Afro-Americans, and Caucasians (Browning M. et al. Immunol Today 1996; 17: 165-170). Therefore, the peptides identified in the present invention which are presented to killer T cells via HLA-A2 have a clinical application potential around the world, if their safety and efficacy in cancer immunotherapy are shown in exploratory-medicine. Further, the identification of peptides that are presented to killer T cells via HLA-A2, bearers of which are frequent not only in Japanese but also in people worldwide, is likely to lead to the development of pharmaceuticals for cancer immunotherapy applicable to about 30% of pancreatic cancer patients around the world.

INDUSTRIAL APPLICABILITY

HLA-A2 is an HLA class I allele carried by about 30% of the Japanese population. When transgenic mice expressing human HLA-A2 are immunized with the CDH3 peptides of the present invention, the peptides can induce cytotoxic T cells that recognize peptides bound to HLA-A2 molecules to induce immune responses. It is highly possible that, also in humans, these peptides can induce human cytotoxic T cells that damage cancer cells expressing complexes of the peptides and HLA-A2 molecules. Therefore, the peptides of the present invention can be applied to immunotherapy for pancreatic cancer, cholangiocellular carcinoma, gastric cancer, colon cancer, and non-small cell lung cancer in HLA-A2 positive patients. Thus, the peptides are expected to improve patients' QOL by suppressing proliferation and/or progress of such cancers.

The invention claimed is:

1. An isolated peptide of the following (A) or (B):
   (A) a peptide consisting of the amino acid sequence of SEQ ID NO: 1 or 2;
   (B) a peptide consisting of the amino acid sequence of SEQ ID NO: 1 or 2, in which one or two amino acid(s) are substituted, wherein the peptide has an activity to induce a cytotoxic (killer) T cell.

2. The peptide of claim 1, wherein the second amino acid from the N-terminus of the amino acid sequence of SEQ ID NO: 1 or 2 is substituted with leucine or methionine.

3. The peptide of claim 1, wherein the C-terminal amino acid of the amino acid sequence of SEQ ID NO: 1 or 2 is substituted with valine or leucine.

4. An agent for inducing immunity against cancer expressing CDH3, comprising one or more peptide(s) of claim 1 as an active ingredient.

5. An agent for treating cancer expressing CDH3, comprising one or more peptide(s) of claim 1 as an active ingredient.

6. An agent for inducing an antigen presenting cell having cytotoxic (killer) T cell-inducing activity, comprising one or more peptide(s) of claim 1 as an active ingredient.

7. An agent for inducing a cytotoxic (killer) T cell, comprising one or more peptide(s) of claim 1 as an active ingredient.

8. A method for inducing an antigen presenting cell having cytotoxic (killer) T cell-inducing activity, comprising a step of contacting an antigen presenting cell with the peptide of claim 1.

9. A method for inducing a cytotoxic (killer) T cell, comprising a step of contacting a T cell with the peptide of claim 1.

10. A method for inducing immunity against cancer expressing CDH3, comprising a step of administering the peptide of claim 1 to a subject.

11. A method for treating cancer expressing CDH3, comprising a step of administering the peptide of claim 1 to a subject.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 1

Phe Ile Leu Pro Val Leu Gly Ala Val
1               5

<210> SEQ ID NO 2
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 2

Phe Ile Ile Glu Asn Leu Lys Ala Ala
1               5

<210> SEQ ID NO 3
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 3

Val Leu Gly Ala Val Leu Ala Leu Leu
1               5

<210> SEQ ID NO 4
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 4

Gln Leu Thr Val Ile Arg Ala Thr Val
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 5

Val Val Leu Ser Leu Lys Lys Phe Leu
1               5

<210> SEQ ID NO 6
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 6

Lys Leu Pro Thr Ser Thr Ala Thr Ile
1               5

<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 7

Val Leu Asn Ile Thr Asp Lys Asp Leu
1               5

<210> SEQ ID NO 8
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 8

Ala Val Ser Glu Asn Gly Ala Ser Val
1               5

<210> SEQ ID NO 9
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 9

Ser Pro Pro Glu Gly Val Phe Ala Val
1               5

<210> SEQ ID NO 10
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 10

Val Leu Pro Gly Thr Ser Val Met Gln Val
1               5                   10

<210> SEQ ID NO 11
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 11
```

Thr Leu Asp Arg Glu Asp Glu Gln Phe Val
1               5                   10

<210> SEQ ID NO 12
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 12

Lys Leu Pro Thr Ser Thr Ala Thr Ile Val
1               5                   10

<210> SEQ ID NO 13
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 13

Phe Val Pro Pro Ser Lys Val Val Glu Val
1               5                   10

<210> SEQ ID NO 14
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 14

Phe Ser Thr Asp Asn Asp Asp Phe Thr Val
1               5                   10

<210> SEQ ID NO 15
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 15

Gly Leu Pro Arg Gly Pro Leu Ala Ser Leu
1               5                   10

<210> SEQ ID NO 16
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 16

Ile Leu Arg Arg His Lys Arg Asp Trp Val
1               5                   10

<210> SEQ ID NO 17
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 17

Ser Val Leu Glu Gly Val Leu Pro Gly Thr

```
                                  -continued
1               5              10

<210> SEQ ID NO 18
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 18

Phe Ile Leu Pro Val Leu Gly Ala Val Leu
1               5              10

<210> SEQ ID NO 19
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 19

Ser Leu Tyr Asn Thr Tyr Ala Thr Leu
1               5
```